United States Patent
Dai et al.

(10) Patent No.: US 9,359,403 B2
(45) Date of Patent: *Jun. 7, 2016

(54) ACTIVATED COLLAGEN SCAFFOLD MATERIALS AND THEIR SPECIAL FUSED ACTIVE RESTORATION FACTORS

(71) Applicants: YANTAI ZHENGHAI BIO-TECHNOLOGY CO., LTD., Shandong (CN); INSTITUTE OF GENETICS AND DEVELOPMENTAL BIOLOGY CHINESE ACADEMY OF SCIENCE, Beijing (CN)

(72) Inventors: Jianwu Dai, Beijing (CN); Bing Chen, Beijing (CN); Hang Lin, Beijing (CN); Wenjie Sun, Beijing (CN); Wenxue Zhao, Beijing (CN)

(73) Assignee: YANTAI ZHENGHAI BIO-TECH CO., LTD, Yantai, Shandong (CN)

( * ) Notice: Subject to any disclaimer, the term of this patent is extended or adjusted under 35 U.S.C. 154(b) by 0 days.

This patent is subject to a terminal disclaimer.

(21) Appl. No.: 14/320,105

(22) Filed: Jun. 30, 2014

(65) Prior Publication Data

US 2014/0316109 A1    Oct. 23, 2014

Related U.S. Application Data

(62) Division of application No. 12/159,369, filed as application No. PCT/CN2006/003244 on Dec. 1, 2006, now Pat. No. 8,802,396.

(30) Foreign Application Priority Data

Dec. 26, 2005    (CN) .......................... 2005 1 0132792
May 24, 2006    (CN) .......................... 2006 1 0081506

(51) Int. Cl.
*C07K 7/06*    (2006.01)
*A61L 27/22*    (2006.01)

(Continued)

(52) U.S. Cl.
CPC ................. *C07K 7/06* (2013.01); *A61L 27/227* (2013.01); *A61L 27/24* (2013.01); *C07K 14/48* (2013.01);

(Continued)

(58) Field of Classification Search
None
See application file for complete search history.

(56) References Cited

U.S. PATENT DOCUMENTS

2005/0250936 A1    11/2005    Oppermann et al.

FOREIGN PATENT DOCUMENTS

| CN | 200510132792.9 | 12/2005 |
| CN | 200610081506.5 | 5/2006 |

(Continued)

OTHER PUBLICATIONS

Andrades et al., "A recombinant human TGF-β1 fusion protein with collagen-binding domain promotes migration, growth, and differentiation of bone marrow mesenchymal cells," *Experimental Cell Research*, 1999, vol. 250, pp. 485-498.

(Continued)

*Primary Examiner* — Alexander Kim
(74) *Attorney, Agent, or Firm* — Knobbe, Martens, Olson & Bear, LLP

(57) ABSTRACT

Provided are activated collagen scaffold materials as well as their special fused active restoration factors useful for promoting tissue repair, such as bone damage repair or nerve injury repair. The special fused active restoration factors are fusion proteins comprising a collagen-binding domain (CBD) at N-/C-terminus of cytokines, wherein the collagen-binding domain is a polypeptide consisting of 7-27 amino acid residues with a conservative sequence shown in SEQ ID NO:12 at N-terminus.

11 Claims, 8 Drawing Sheets

(51) Int. Cl.
  A61L 27/24    (2006.01)
  C07K 14/48    (2006.01)
  C07K 14/485   (2006.01)
  C07K 14/49    (2006.01)
  C07K 14/50    (2006.01)
  C07K 14/51    (2006.01)
  C07K 14/52    (2006.01)
  C07K 14/78    (2006.01)
  A61K 38/00    (2006.01)

(52) U.S. Cl.
  CPC ............... *C07K 14/485* (2013.01); *C07K 14/49* (2013.01); *C07K 14/503* (2013.01); *C07K 14/51* (2013.01); *C07K 14/52* (2013.01); *C07K 14/78* (2013.01); *A61K 38/00* (2013.01); *C07K 2319/00* (2013.01); *C07K 2319/21* (2013.01)

(56) References Cited

FOREIGN PATENT DOCUMENTS

| | | |
|---|---|---|
| CN | 1807459 A | 7/2006 |
| EP | 1 357 130 A1 | 10/2003 |
| WO | WO 00/06195 A1 | 2/2000 |
| WO | WO 01/07059 A1 | 2/2001 |
| WO | WO 02/42331 A1 | 5/2002 |

OTHER PUBLICATIONS

Andrades et al., "Engineering, expression, and renaturation of a collagen-targeted human bFGF fusion protein," *Growth Factors*, 2001, vol. 18(4), pp. 261-75.

De Souza et al., "Collagen binding site in collagenase can be determined using the concept of sense-antisense peptide Interactions," *Journal of Biological Chemistry*, 1992, vol. 267, pp. 13763-13767.

Geiger et al., "Collagen sponges for bone regeneration with rhBMP-2," *Advanced Drug Delivery Reviews*, 2003, vol. 55, pp. 1613-1629.

Hall et al., "Design, expression, and renaturation of a lesion-targeted recombinant epidermal growth factor-van Willebrand factor fusion protein: efficacy in an animal model of experimental colitis," *Int J Mol Med*, 2000, vol. 6, pp. 635-678.

Han et al., "Refolding of a Recombinant Collagen-Targeting TGF-β2 Fusion Protein Expressed in *Escherichia coli*," *Protein Expression and Purification* (1997), vol. 11, pp. 169-178.

Ishikawa et al., "Production of a Biologically Action Epidermal Growth Factors Fusion Protein with High Collagen Affinity," *J. Biochem*, 2001, vol. 129, pp. 627-633.

Lin et al., "The effect of collagen-targeting platelet-derived growth factor on cellularization and vascularization of collagen scaffolds," *Biomaterials*, 2006, vol. 27, pp. 5708-5714.

Nishi et al., "Collagen-binding growth factors: production and characterization of functional fusion proteins having a collagen-binding domain," *Proc. Natl. Acad. Sci. USA*, 1998, vol. 95, pp. 7018-7023.

Zhao et al., "Vascularization and cellularization of collagen scaffolds incorporated with two different collagen-targeting human basic fibroblast growth factors," *J Biomed Mat Research Part A*, 2007, vol. 82, Issue 3, pp. 630-636.

Chen, Bing, et al. "Homogeneous osteogenesis and bone regeneration by demineralized bone matrix loading with collagen-targeting bone morphogenetic protein-2." Biomaterials 28.6 (2007): 1027-1035.

Chen, Bing, et al. "Activation of demineralized bone matrix by genetically engineered human bone morphogenetic protein-2 with a collagen binding domain derived from von Willebrand factor propolypeptide." Journal of Biomedical Materials Research Part A 80.2 (2007): 428-434.

Chen, Wei, et al "Bladder regeneration by collagen scaffolds with collagen binding human basic fibroblast growth factor." *The Journal of urology* 183.6 (2010): 2432-2439.

Zhao, Wenxue, et al. "Vascularization and cellularization of collagen scaffolds incorporated with two different collagen-targeting human basic fibroblast growth factors." Journal of Biomedical Materials Research Part A 82.3 (2007): 630-636.

Sun, Wenjie, et al. "Promotion of peripheral nerve growth by collagen scaffolds loaded with collagen-targeting human nerve growth factor-β." Journal of biomedical materials research Part A 83.4 (2007): 1054-1061.

Sun, Wenjie, et al. "The effect of collagen-binding NGF-β on the promotion of sciatic nerve regeneration in a rat sciatic nerve crush injury model." Biomaterials 30.27 (2009): 4649-4656.

Sun, Wenjie, et al. "Collagen scaffolds loaded with collagen-binding NGF-β accelerate ulcer healing." Journal of biomedical materials research Part A 92.3 (2010): 887-895.

Shi, Chunying, et al. "Regeneration of full-thickness abdominal wall defects in rats using collagen scaffolds loaded with collagen-binding basic fibroblast growth factor." Biomaterials 32.3 (2011): 753-759.

Li, Xin'An, et al. "Regeneration of uterine horns in rats by collagen scaffolds loaded with collagen-binding human basic fibroblast growth factor." Biomaterials 32.32 (2011): 8172-8181.

Li, Qiang, et al. "Extrahepatic bile duct regeneration in pigs using collagen scaffolds loaded with human collagen-binding bFGF." Biomaterials 33.17 (2012): 4298-4308.

Han, Q., et al "Evaluation of a bioactive bone-inducing material consisting of collagen scaffolds and collagen-binding BMP2." J Biomed Mater Res Part A 2014:102A:3093-3101.

SEQUENCE LISTING

<160> NUMBER OF SEQ ID NOS: 30

<210> SEQ ID NO 1
<211> LENGTH: 7
<212> TYPE: PRT
<213> ORGANISM: Artificial Sequence

```
<220> FEATURE:
<223> OTHER INFORMATION: Synthetic Peptide

<400> SEQUENCE: 1

Thr Lys Lys Thr Leu Arg Thr
1               5

<210> SEQ ID NO 2
<211> LENGTH: 157
<212> TYPE: PRT
<213> ORGANISM: Artificial Sequence
<220> FEATURE:
<223> OTHER INFORMATION: Fusion Peptide

<400> SEQUENCE: 2

Met Gly Ser Ser His His His His His His Ser Gly Leu Val Pro
1               5                   10                  15

Arg Gly Ser His Met Thr Lys Lys Thr Leu Arg Thr Gly Thr Gly Ser
                20                  25                  30

Ala Gly Ser Ala Ala Gly Ser Gly Gly Val Asp Gln Ala Lys His Lys
            35                  40                  45

Gln Arg Lys Arg Leu Lys Ser Ser Cys Lys Arg His Pro Leu Tyr Val
50                  55                  60

Asp Phe Ser Asp Val Gly Trp Asn Asp Trp Ile Val Ala Pro Pro Gly
65                  70                  75                  80

Tyr His Ala Phe Tyr Cys His Gly Glu Cys Pro Phe Pro Leu Ala Asp
                85                  90                  95

His Leu Asn Ser Thr Asn His Ala Ile Val Gln Thr Leu Val Asn Ser
            100                 105                 110

Val Asn Ser Lys Ile Pro Lys Ala Cys Cys Val Pro Thr Glu Leu Ser
        115                 120                 125

Ala Ile Ser Met Leu Tyr Leu Asp Glu Asn Glu Lys Val Val Leu Lys
130                 135                 140

Asn Tyr Gln Asp Met Val Val Glu Gly Cys Gly Cys Arg
145                 150                 155

<210> SEQ ID NO 3
<211> LENGTH: 477
<212> TYPE: DNA
<213> ORGANISM: Artificial Sequence
<220> FEATURE:
<223> OTHER INFORMATION: Fusion peptide construct

<400> SEQUENCE: 3
atgggcagca gccatcatca tcatcatcac agcagcggcc tggtgccgcg cggcagccat      60
atgactaaga aaaccctgcg tactggtacc ggtagcgcgg cagtgctgc gggttctggc     120 ggtgtcgacc aagccaaaca caaacagcgg aaacgcctta agtccagctg taagagacac     180
cctttgtacg tggacttcag tgacgtgggg tggaatgact ggattgtggc tcccccgggg     240
tatcacgcct tttactgcca cggagaatgc ccttttcctc tggctgatca tctgaactcc     300
actaatcatg ccattgttca gacattggtc aactctgtta actctaagat tcctaaggca     360
tgctgtgtcc cgacagaact cagtgctatc tcgatgctgt accttgacga gaatgaaaag     420
gttgtattaa agaactatca ggacatggtt gtggagggtt gtggttgtcg ttaatag       477

<210> SEQ ID NO 4
<211> LENGTH: 159
<212> TYPE: PRT
<213> ORGANISM: Artificial Sequence
```

<220> FEATURE:
<223> OTHER INFORMATION: Fusion peptide

<400> SEQUENCE: 4

```
Met Gly Ser Ser His His His His His Ser Ser Gly Leu Val Pro
1               5                   10                  15

Arg Gly Ser His Met Thr Lys Lys Thr Leu Arg Thr Gly Ser Ala Gly
            20                  25                  30

Ser Ala Ala Gly Ser Gly Gly Lys Leu Ser Ser Ser His Pro Ile Phe
        35                  40                  45

His Arg Gly Glu Phe Ser Val Cys Asp Ser Val Ser Val Trp Val Gly
    50                  55                  60

Asp Lys Thr Thr Ala Thr Asp Ile Lys Gly Lys Glu Val Met Val Leu
65                  70                  75                  80

Gly Glu Val Asn Ile Asn Asn Ser Val Phe Lys Gln Tyr Phe Phe Glu
                85                  90                  95

Thr Lys Cys Arg Asp Pro Asn Pro Val Asp Ser Gly Cys Arg Gly Ile
            100                 105                 110

Asp Ser Lys His Trp Asn Ser Tyr Cys Thr Thr Thr His Thr Phe Val
        115                 120                 125

Lys Ala Leu Thr Met Asp Gly Lys Gln Ala Ala Trp Arg Phe Ile Arg
    130                 135                 140

Ile Asp Thr Ala Cys Val Cys Val Leu Ser Arg Lys Ala Val Arg
145                 150                 155
```

<210> SEQ ID NO 5
<211> LENGTH: 480
<212> TYPE: DNA
<213> ORGANISM: Artificial Sequence
<220> FEATURE:
<223> OTHER INFORMATION: Fusion peptide construct

<400> SEQUENCE: 5

```
atgggcagca gccatcatca tcatcatcac agcagcggcc tggtgccgcg cggcagccat      60
atgactaaga aaaccctgcg tactggtagc gcgggcagtg ctgcgggttc tggcggtaag     120
ctttcatcat cccatcccat cttccacagg ggcgaattct cggtgtgtga cagtgtcagc     180
gtgtgggttg gggataagac caccgccaca gacatcaagg gcaaggaggt gatggtgttg     240
ggagaggtga acattaacaa cagtgtattc aaacagtact ttttgagac caagtgccgg      300
gacccaaatc ccgttgacag cgggtgccgg ggcattgact caaagcactg gaactcatat     360
tgtaccacga ctcacacctt tgtcaaggcg ctgaccatgg atggcaagca ggctgcctgg     420
cggtttatcc ggatagatac ggcctgtgtg tgtgtgctca gcaggaaggc tgtgagatga     480
```

<210> SEQ ID NO 6
<211> LENGTH: 139
<212> TYPE: PRT
<213> ORGANISM: Artificial Sequence
<220> FEATURE:
<223> OTHER INFORMATION: Fusion peptide

<400> SEQUENCE: 6

```
Met Gly Ser Ser His His His His His Ser Ser Gly Leu Val Pro
1               5                   10                  15

Arg Gly Ser His Met Ser Ser Ser His Pro Ile Phe His Arg Gly Glu
            20                  25                  30

Phe Ser Val Cys Asp Ser Val Ser Val Trp Val Gly Asp Lys Thr Thr
        35                  40                  45
```

```
Ala Thr Asp Ile Lys Gly Lys Glu Val Met Val Leu Gly Glu Val Asn
    50                  55                  60
Ile Asn Asn Ser Val Phe Lys Gln Tyr Phe Glu Thr Lys Cys Arg
 65                  70                  75                  80
Asp Pro Asn Pro Val Asp Ser Gly Cys Arg Gly Ile Asp Ser Lys His
                 85                  90                  95
Trp Asn Ser Tyr Cys Thr Thr Thr His Thr Phe Val Lys Ala Leu Thr
                100                 105                 110
Met Asp Gly Lys Gln Ala Ala Trp Arg Phe Ile Arg Ile Asp Thr Ala
            115                 120                 125
Cys Val Cys Val Leu Ser Arg Lys Ala Val Arg
130                 135
```

<210> SEQ ID NO 7
<211> LENGTH: 420
<212> TYPE: DNA
<213> ORGANISM: Artificial Sequence
<220> FEATURE:
<223> OTHER INFORMATION: Fusion peptide construct

<400> SEQUENCE: 7

```
atgggcagca gccatcatca tcatcatcac agcagcggcc tggtgccgcg cggcagccat     60
atgtcatcat cccatcccat cttccacagg ggcgaattct cggtgtgtga cagtgtcagc    120
gtgtgggttg gggataagac caccgccaca gacatcaagg gcaaggaggt gatggtgttg    180
ggagaggtga acattaacaa cagtgtattc aaacagtact tttttgagac caagtgccgg    240
gacccaaatc ccgttgacag cgggtgccgg ggcattgact caaagcactg gaactcatat    300
tgtaccacga ctcacacctt tgtcaaggcg ctgaccatgg atggcaagca ggctgcctgg    360
cggtttatcc ggatagatac ggcctgtgtg tgtgtgctca gcaggaaggc tgtgagatga    420
```

<210> SEQ ID NO 8
<211> LENGTH: 150
<212> TYPE: PRT
<213> ORGANISM: Artificial Sequence
<220> FEATURE:
<223> OTHER INFORMATION: Fusion peptide

<400> SEQUENCE: 8

```
Met Gly Ser Ser His His His His His His Ser Ser Gly Leu Val Pro
  1               5                  10                  15
Arg Gly Ser His Met Thr Lys Lys Thr Leu Arg Thr Gly Ser Ala Gly
             20                  25                  30
Ser Ala Ala Gly Ser Gly Gly Val Asp Ser Leu Gly Ser Leu Thr Ile
         35                  40                  45
Ala Glu Pro Ala Met Ile Ala Glu Cys Lys Thr Arg Thr Glu Val Phe
    50                  55                  60
Glu Ile Ser Arg Arg Leu Ile Asp Arg Thr Asn Ala Asn Phe Leu Val
 65                  70                  75                  80
Trp Pro Pro Cys Val Glu Val Gln Arg Cys Ser Gly Cys Cys Asn Asn
                 85                  90                  95
Arg Asn Val Gln Cys Arg Pro Thr Gln Val Gln Leu Arg Pro Val Gln
                100                 105                 110
Val Arg Lys Ile Glu Ile Val Arg Lys Lys Pro Ile Phe Lys Lys Ala
            115                 120                 125
Thr Val Thr Leu Glu Asp His Leu Ala Cys Lys Cys Glu Thr Val Ala
        130                 135                 140
```

Ala Ala Arg Pro Val Thr
145                 150

<210> SEQ ID NO 9
<211> LENGTH: 453
<212> TYPE: DNA
<213> ORGANISM: Artificial Sequence
<220> FEATURE:
<223> OTHER INFORMATION: Fusion peptide construct

<400> SEQUENCE: 9

```
atgggcagca gccatcatca tcatcatcac agcagcggcc tggtgccgcg cggcagccat      60
atgactaaga aaaccctgcg tactggtagc gcgggcagtg ctgcgggttc tggcggtaag     120
cttagcctgg gttccctgac cattgctgag ccggccatga tcgccgagtg caagacgcgc     180
accgaggtgt tcgagatctc ccggcgcctc atagaccgca ccaacgccaa cttcctggtg     240
tggccgccct gtgtggaggt gcagcgctgc tccggctgct gcaacaaccg caacgtgcag     300
tgccgcccca cccaggtgca gctgcgacct gtccaggtga aaagatcga gattgtgcgg     360
aagaagccaa tctttaagaa ggccacggtg acgctggaag accacctggc atgcaagtgt     420
gagacagtgg cagctgcacg gcctgtgacc tga                                  453
```

<210> SEQ ID NO 10
<211> LENGTH: 130
<212> TYPE: PRT
<213> ORGANISM: Artificial Sequence
<220> FEATURE:
<223> OTHER INFORMATION: Fusion peptide

<400> SEQUENCE: 10

Met Gly Ser Ser His His His His His Ser Ser Gly Leu Val Pro
1               5                   10                  15

Arg Gly Ser His Met Ser Leu Gly Ser Leu Thr Ile Ala Glu Pro Ala
            20                  25                  30

Met Ile Ala Glu Cys Lys Thr Arg Thr Glu Val Phe Glu Ile Ser Arg
        35                  40                  45

Arg Leu Ile Asp Arg Thr Asn Ala Asn Phe Leu Val Trp Pro Pro Cys
    50                  55                  60

Val Glu Val Gln Arg Cys Ser Gly Cys Cys Asn Asn Arg Asn Val Gln
65                  70                  75                  80

Cys Arg Pro Thr Gln Val Gln Leu Arg Pro Val Gln Val Arg Lys Ile
                85                  90                  95

Glu Ile Val Arg Lys Lys Pro Ile Phe Lys Lys Ala Thr Val Thr Leu
            100                 105                 110

Glu Asp His Leu Ala Cys Lys Cys Glu Thr Val Ala Ala Ala Arg Pro
        115                 120                 125

Val Thr
    130

<210> SEQ ID NO 11
<211> LENGTH: 393
<212> TYPE: DNA
<213> ORGANISM: Artificial Sequence
<220> FEATURE:
<223> OTHER INFORMATION: Fusion peptide construct

<400> SEQUENCE: 11

```
atgggcagca gccatcatca tcatcatcac agcagcggcc tggtgccgcg cggcagccat      60
```

| | |
|---|---|
| atgagcctgg gttccctgac cattgctgag ccggccatga tcgccgagtg caagacgcgc | 120 |
| accgaggtgt tcgagatctc ccggcgcctc atagaccgca ccaacgccaa cttcctggtg | 180 |
| tggccgccct gtgtggaggt gcagcgctgc tccggctgct gcaacaaccg caacgtgcag | 240 |
| tgccgcccca cccaggtgca gctgcgacct gtccaggtga aaagatcga gattgtgcgg | 300 |
| aagaagccaa tctttaagaa ggccacggtg acgctggaag accacctggc atgcaagtgt | 360 |
| gagacagtgg cagctgcacg gcctgtgacc tga | 393 |

```
<210> SEQ ID NO 12
<211> LENGTH: 197
<212> TYPE: PRT
<213> ORGANISM: Artificial Sequence
<220> FEATURE:
<223> OTHER INFORMATION: Fusion peptide

<400> SEQUENCE: 12

Met Gly Ser Ser His His His His His His Ser Ser Gly Leu Val Pro
1               5                   10                  15

Arg Gly Ser His Met Thr Lys Lys Thr Leu Arg Thr Gly Thr Gly Ser
                20                  25                  30

Ala Gly Ser Ala Ala Gly Ser Gly Gly Val Asp Ala Ala Gly Ser Ile
            35                  40                  45

Thr Thr Leu Pro Ala Leu Pro Glu Asp Gly Gly Ser Gly Ala Phe Pro
    50                  55                  60

Pro Gly His Phe Lys Asp Pro Lys Arg Leu Tyr Cys Lys Asn Gly Gly
65                  70                  75                  80

Phe Phe Leu Arg Ile His Pro Asp Gly Arg Val Asp Gly Val Arg Glu
                85                  90                  95

Lys Ser Asp Pro His Ile Lys Leu Gln Leu Gln Ala Glu Glu Arg Gly
            100                 105                 110

Val Val Ser Ile Lys Gly Val Cys Ala Asn Arg Tyr Leu Ala Met Lys
        115                 120                 125

Glu Asp Gly Arg Leu Leu Ala Ser Lys Cys Val Thr Asp Glu Cys Phe
    130                 135                 140

Phe Phe Glu Arg Leu Glu Ser Asn Asn Tyr Asn Thr Tyr Arg Ser Arg
145                 150                 155                 160

Lys Tyr Thr Ser Trp Tyr Val Ala Leu Lys Arg Thr Gly Gln Tyr Lys
                165                 170                 175

Leu Gly Ser Lys Thr Gly Pro Gly Gln Lys Ala Ile Leu Phe Leu Pro
            180                 185                 190

Met Ser Ala Lys Ser
        195

<210> SEQ ID NO 13
<211> LENGTH: 591
<212> TYPE: DNA
<213> ORGANISM: Artificial Sequence
<220> FEATURE:
<223> OTHER INFORMATION: Fusion peptide construct

<400> SEQUENCE: 13
```

| | |
|---|---|
| atgggcagca gccatcatca tcatcatcac agcagcggcc tggtgccgcg cggcagccat | 60 |
| atgactaaga aaaccctgcg tactggtacc ggtagcgcgg cagtgctgc gggttctggc | 120 |
| ggtgtcgacg cagccgggag catcaccacg ctgcccgcct tgcccgagga tggcggcagc | 180 |
| ggcgccttcc cgcccggcca cttcaaggac cccaagcggc tgtactgcaa aaacggggc | 240 |

```
ttcttcctgc gcatccaccc cgacggccga gttgacgggg tccggagaa gagcgaccct      300 cacatcaagc tacaacttca agcagaagag agaggagttg tgtctatcaa aggagtgtgt      360
gctaaccgtt acctggctat gaaggaagat ggaagattac tggcttctaa atgtgttacg      420
gatgagtgtt tctttttga acgattggaa tctaataact acaatactta ccggtcaagg      480
aaatacacca gttggtatgt ggcactgaaa cgaactgggc agtataaact tggatccaaa      540
acaggacctg gcagaaagc tatactttt cttccaatgt ctgctaagag c               591
```

<210> SEQ ID NO 14
<211> LENGTH: 175
<212> TYPE: PRT
<213> ORGANISM: Artificial Sequence
<220> FEATURE:
<223> OTHER INFORMATION: Fusion peptide

<400> SEQUENCE: 14

```
Met Gly Ser Ser His His His His His His Ser Ser Gly Leu Val Pro
1               5                   10                  15

Arg Gly Ser His Met Ala Ala Gly Ser Ile Thr Thr Leu Pro Ala Leu
            20                  25                  30

Pro Glu Asp Gly Gly Ser Gly Ala Phe Pro Pro Gly His Phe Lys Asp
        35                  40                  45

Pro Lys Arg Leu Tyr Cys Lys Asn Gly Gly Phe Phe Leu Arg Ile His
    50                  55                  60

Pro Asp Gly Arg Val Asp Gly Val Arg Glu Lys Ser Asp Pro His Ile
65                  70                  75                  80

Lys Leu Gln Leu Gln Ala Glu Glu Arg Gly Val Val Ser Ile Lys Gly
                85                  90                  95

Val Cys Ala Asn Arg Tyr Leu Ala Met Lys Glu Asp Gly Arg Leu Leu
            100                 105                 110

Ala Ser Lys Cys Val Thr Asp Glu Cys Phe Phe Phe Glu Arg Leu Glu
        115                 120                 125

Ser Asn Asn Tyr Asn Thr Tyr Arg Ser Arg Lys Tyr Thr Ser Trp Tyr
    130                 135                 140

Val Ala Leu Lys Arg Thr Gly Gln Tyr Lys Leu Gly Ser Lys Thr Gly
145                 150                 155                 160

Pro Gly Gln Lys Ala Ile Leu Phe Leu Pro Met Ser Ala Lys Ser
                165                 170                 175
```

<210> SEQ ID NO 15
<211> LENGTH: 525
<212> TYPE: DNA
<213> ORGANISM: Artificial Sequence
<220> FEATURE:
<223> OTHER INFORMATION: Fusion peptide construct

<400> SEQUENCE: 15

```
atgggcagca gccatcatca tcatcatcac agcagcggcc tggtgccgcg cggcagccat      60
atggcagccg ggagcatcac cacgctgccc gccttgcccg aggatggcgg cagcggcgcc     120
ttcccgcccg gccacttcaa ggaccccaag cggctgtact gcaaaaacgg gggcttcttc     180
ctgcgcatcc accccgacgg ccgagttgac ggggtccggg agaagagcga ccctcacatc     240
aagctacaac ttcaagcaga agagagagga gttgtgtcta tcaaggagt gtgtgctaac     300 cgttacctgg ctatgaagga agatggaaga ttactggctt ctaaatgtgt tacggatgag     360
tgtttctttt ttgaacgatt ggaatctaat aactacaata cttaccggtc aaggaaatac     420
```

```
accagttggt atgtggcact gaaacgaact gggcagtata aacttggatc caaaacagga      480
cctgggcaga aagctatact ttttcttcca atgtctgcta agagc                     525

<210> SEQ ID NO 16
<211> LENGTH: 55
<212> TYPE: DNA
<213> ORGANISM: Artificial Sequence
<220> FEATURE:
<223> OTHER INFORMATION: oligonucleotide primer

<400> SEQUENCE: 16
taccggtagc gcgggcagtg ctgcgggttc tggcggtgtc gaccaagcca aacac           55

<210> SEQ ID NO 17
<211> LENGTH: 42
<212> TYPE: DNA
<213> ORGANISM: Artificial Sequence
<220> FEATURE:
<223> OTHER INFORMATION: oligonucleotide primer

<400> SEQUENCE: 17
ccgcatatga ctaagaaaac cctgcgtact ggtaccggta gc                         42

<210> SEQ ID NO 18
<211> LENGTH: 30
<212> TYPE: DNA
<213> ORGANISM: Artificial Sequence
<220> FEATURE:
<223> OTHER INFORMATION: oligonucleotide primer

<400> SEQUENCE: 18
ccgctcgagc tattaacgac aaccacaacc                                       30

<210> SEQ ID NO 19
<211> LENGTH: 45
<212> TYPE: DNA
<213> ORGANISM: Artificial Sequence
<220> FEATURE:
<223> OTHER INFORMATION: oligonucleotide primer

<400> SEQUENCE: 19
atccatatga ctaagaaaac cctgcgtact ggtagcgcgg gcagt                      45

<210> SEQ ID NO 20
<211> LENGTH: 45
<212> TYPE: DNA
<213> ORGANISM: Artificial Sequence
<220> FEATURE:
<223> OTHER INFORMATION: oligonucleotide primer

<400> SEQUENCE: 20
actaagctta ccgccagaac ccgcagcact gcccgcgcta ccagt                      45

<210> SEQ ID NO 21
<211> LENGTH: 33
<212> TYPE: DNA
<213> ORGANISM: Artificial Sequence
<220> FEATURE:
<223> OTHER INFORMATION: oligonucleotide primer

<400> SEQUENCE: 21
ctacatatgt cttcgtccca tcccatcttc cac                                   33

<210> SEQ ID NO 22
<211> LENGTH: 33
```

```
<212> TYPE: DNA
<213> ORGANISM: Artificial Sequence
<220> FEATURE:
<223> OTHER INFORMATION: oligonucleotide primer

<400> SEQUENCE: 22
gctaagcttt cttcgtccca tcccatcttc cac                              33

<210> SEQ ID NO 23
<211> LENGTH: 36
<212> TYPE: DNA
<213> ORGANISM: Artificial Sequence
<220> FEATURE:
<223> OTHER INFORMATION: oligonucleotide primer

<400> SEQUENCE: 23
gatctcgagt catctcacag ccttcctgct gagcac                           36

<210> SEQ ID NO 24
<211> LENGTH: 12
<212> TYPE: PRT
<213> ORGANISM: Artificial Sequence
<220> FEATURE:
<223> OTHER INFORMATION: Synthetic peptide

<400> SEQUENCE: 24

Gly Ser Ala Gly Ser Ala Ala Gly Ser Gly Gly Lys
1               5                   10

<210> SEQ ID NO 25
<211> LENGTH: 31
<212> TYPE: DNA
<213> ORGANISM: Artificial Sequence
<220> FEATURE:
<223> OTHER INFORMATION: oligonucleotide primer

<400> SEQUENCE: 25
ctacatatga gcctgggttc cctgaccatt g                                31

<210> SEQ ID NO 26
<211> LENGTH: 31
<212> TYPE: DNA
<213> ORGANISM: Artificial Sequence
<220> FEATURE:
<223> OTHER INFORMATION: oligonucleotide primer

<400> SEQUENCE: 26
gctaagctta gcctgggttc cctgaccatt g                                31

<210> SEQ ID NO 27
<211> LENGTH: 34
<212> TYPE: DNA
<213> ORGANISM: Artificial Sequence
<220> FEATURE:
<223> OTHER INFORMATION: oligonucleotide primer

<400> SEQUENCE: 27
gatctcgagt caggtcacag gccgtgcagc tgcc                             34

<210> SEQ ID NO 28
<211> LENGTH: 21
<212> TYPE: DNA
<213> ORGANISM: Artificial Sequence
<220> FEATURE:
<223> OTHER INFORMATION: oligonucleotide primer

<400> SEQUENCE: 28
```

```
ggtaccggta gcgcgggcag t                                              21

<210> SEQ ID NO 29
<211> LENGTH: 27
<212> TYPE: DNA
<213> ORGANISM: Artificial Sequence
<220> FEATURE:
<223> OTHER INFORMATION: oligonucleotide primer

<400> SEQUENCE: 29
gtcgacgcag ccgggagcat caccacg                                        27

<210> SEQ ID NO 30
<211> LENGTH: 31
<212> TYPE: DNA
<213> ORGANISM: Artificial Sequence
<220> FEATURE:
<223> OTHER INFORMATION: oligonucleotide primer

<400> SEQUENCE: 30
ctcgaggctc ttagcagaca ttggaagaaa a                                   31
```

ACTIVATED COLLAGEN SCAFFOLD MATERIALS AND THEIR SPECIAL FUSED ACTIVE RESTORATION FACTORS

This application is a divisional of U.S. patent application Ser. No. 12/159,369, filed Sep. 29, 2008, which is a U.S. National Phase of International Application PCT/CN2006/003244, filed Dec. 1, 2006 designating the U.S., which claims priority to Chinese Patent Application No. 200510132792.9, filed Dec. 26, 2005 and Chinese Patent Application No. 200610081506.5, filed May 24, 2006.

REFERENCE TO SEQUENCE LISTING

A Sequence Listing submitted as an ASCII text file via EFS-Web is hereby incorporated by reference in accordance with 35 U.S.C. §1.52(e). The name of the ASCII text file for the Sequence Listing is 11894039_1.txt, the date of creation of the ASCII text file is Sep. 10, 2011, and the size of the ASCII text file is 20 KB.

FIELD OF THE INVENTION

The present invention is related to activated collagen scaffold materials and fused active restoration factors with the ability to specifically bind collagens.

BACKGROUND

Cytokine is a general term for cell-secreted small proteins with biological activities. In many circumstances, the interactions among various immune cells are mediated by cytokines.

Among these cytokines, nerve growth factor (NGF) is a complex consisting of three different subunits, α, β, and γ, with a molecular weight of about 140 Kd. Researches show that the β subunit of NGF is a homodimer, with a single chain of 118 amino acid residues (Greene, L. A. and E. M. Shooter, *The nerve growth factor: biochemistry, synthesis, and mechanism of action.* Annu Rev Neurosci, 1980. 3: p. 353-402). The β subunit, the functional subunit of NGF, is in close association with many aspects, such as neuron survival, migration, growth, and differentiation, as well as establishing functional connections with other cells, and the like; has the dual functions of neurotrophy and neurite promoting; and is one of the most important biological active substances in nervous system. In addition, it also plays a vital role in preventing denervation muscle atrophy (Sofroniew, M. V., C. L. Howe, and W. C. Mobley, *Nerve growth factor signaling, neuroprotection, and neural repair.* Annu Rev Neurosci, 2001. 24: p. 1217-81). Clinical applications confirmed that local administration can enable nerves to obtain nutrition directly, which is beneficial for the axoplasmic flow of nerves, promoting nerve regeneration. Currently, the major administration methods for treating peripheral nerve injuries using neurotrophic factors are as follows: (1) direct administration at a local injury; (2) slow releasing administration by micro-osmotic pump at a local injury; and (3) transplanting cells expressing neurotrophic factors to a local injury via a transgenic technique. Application of exogenous β-NGF in vivo by means of direct administration is affected by many factors. The sustaining of its activity and its effect are associated with administration routes, modes and dosage. Single dose administration can barely ensure the continuous action of medicines, whereas successive administration requires a large amount of medicines, its treatment cost is very large, and its safety becomes a concern due to the large quantity of NGF. Micro-osmotic pump has problems of a rejection reaction and a poor absorption in vivo. The vector selection and safety issues for gene therapy are difficult to resolve. Therefore, all the administration methods mentioned above are difficult to apply NGF clinically.

Platelet-derived growth factor (PDGF-BB) is a peptide growth factor produced by various cell (e.g. platelet, mononuclear macrophage, vascular endothelial cell, vascular smooth muscle cell, placental and embryonic cells, mesangial cell and so on), and its biological properties are mainly showed as: 1) cell division promoting effects, capable of stimulating meiosis of various cells (e.g. vascular smooth muscle cells, fibroblasts, endothelial cells and glial cells), and regulating the renewal of extracellular matrix by stimulating collagen synthesis and activating the collagenase; 2) chemotaxis towards fibroblasts, smooth muscle cells and neutrophilic granulocytes; and 3) vasoconstriction effects. PDGF-BB plays an important role in cell culture, the treatment of skin ulcer, and the preparation of cosmetic additives. Currently, application in vivo of exogenous β-NGF by means of direct administration is affected by many factors. The sustaining of its activity and its effect are associated with routes, modes and dosage of administration. Single dose administration can barely ensure the continuous action of medicines whereas successive administration requires a large amount of medicines, its treatment cost is very large, and its safety becomes a concern due to the large quantity of PDGF-BB used.

Basic fibroblast growth factor (bFGF) is a multi-function peptide growth factor with the functions of promoting proliferation, migration and differentiation of various cells. It not only plays an important role in the early development of embryo, but also can promote the restoration of adult injury, and thereby is used for treating body injuries. Now, there are genetic engineered bFGFs on the market, which have been approved by the Department of Health, showing therapeutic values. However, current bFGFs used clinically all have the following defects: 1) easy to diffuse and invade into other tissues, causing injured sites not to be restored as desired, and other normal tissues to face potential safety issue, with increases in dosage and cost; and 2) a short half-life, easy to lose activity in vivo, causing decreased treatment effects.

Bone defects caused by injury, infection, tumor, and dysplasia are the problems encountered daily in clinical orthopaedics. Bone morphogenetic protein (BMP) belongs to transforming growth factor β superfamily. It can induce new bone formation in non-bone tissues (e.g. muscle), and thus is very important in bone growth and treatments of bone defects. BMP family includes at least 20 members, wherein human bone morphogenetic protein (BMP2) has a strong osteoinductive activity. Human BMP2 is a glycosylated protein of 396 amino acid residues in full length, including a signal peptide comprised of 19 amino acid residues, a pro-region consisting of 263 amino acid residues, and a mature peptide consisting of 114 amino acid residues. The mature peptide comprises seven cysteine residues and one N-glycosylation site, and its functional form is a homodimer formed through a pair of disulfide bond, the remaining six cysteine residues in each monomer forming three intrachain disulfide bonds (Wozney, J. M. et al. Novel regulators of bone formation: molecular clones and activities. Science 242, 1528-34, 1988). However, the content of natural BMP2 is very low, and isolation and purification of BMP2 from human and animal bones are of great limitations. At present, studies are focused on preparing recombinant BMP2 by means of genetic engineering, in order to meet the demands of clinical and fundamental researches. In addition, other factors functionally similar to BMP2, which can induce tissue regeneration and injury restoration, further include: BMP3, PDGF, FGF, EGF, TGF, VEGF, NGF, NT3/4 and the like.

Collagen, one of the major components of extracellular matrix of neurons, constitutes the scaffold for neuron growth together with other extracellular matrix. Combined with PDGF, Collagen is often used for treating skin injuries, such as ulcer. Additionally, collagen is a commonly used bone restoration material. It is a major organic component of bones, wherein type I collagen and its crosslinked fiber structure are the most abundant proteins within the extracellular matrix. Collagen structures can induce mineral deposition. There are mineral deposition sites on its surface, which can effectively induce and control the process of mineralization, promote bone formation, and induce it into implants. Via the molecular structures of collagen molecules, conventional collagen carriers prevent BMP2 component from diffusing and maintain the BMP2 concentration around host target cells. As such, on one hand, it is required that their pore sizes should not be too large. However, too small pore size is not good for the growth of osteoblasts, which requires the control of a range of pore sizes, introducing some difficulties in technology. On the other hand, the use of current biological materials as BMP2 carriers causes large dose of BMP2, usually up to a level of milligrams (see, Kirker-Head, C. A., Gerhart, T. N., Armstrong, R., Schelling, S. H. & Carmel, L. A. Healing bone using recombinant human bone morphogenetic protein 2 and copolymer. Clin. Orthop. Relat. Res., 205-17 (1998); Kokubo, S. et al. Bone regeneration by recombinant human bone morphogenetic protein-2 and a novel biodegradable carrier in a rabbit ulnar defect model. Biomaterials 24, 1643-51 (2003)). Since the commercially available BMP2 at present is very expensive, for example, the price of BMP2 available from Sigma for experimental research purposes reached US$ 500/10 µg, and few domestic patients can afford it. Moreover, several milligrams (mg) of BMP2s are equivalent to the total amount of BMP2 extracted from a bovine, and the safety issue becomes a concern due to the use of the large amount of BMP2.

DISCLOSURE OF THE INVENTION

One object of the present invention is to provide a fused active restoration factors having the ability of specifically binding to collagen, which can be used to activate collagen scaffold material for injury restoration.

The fused active restoration factors provided by the present invention, used to activate collagen scaffold material for injury restoration, are fusion proteins obtained by fusing a collagen binding domain (CBD) to the amino terminus (N-terminus) or carboxyl terminus (C-terminus) of cytokines, wherein the collagen binding domain is a protein consisting of 7-27 amino acid residues, with the first 7 amino acid residues from its amino terminus as set forth in SEQ ID NO:1 being its conserved sequence.

SEQ ID NO:1 in the Sequence Listing consists of 7 amino acid residues.

The amino acid residues in the CBD, other than the conserved sequence, may be optionally selected without affecting its activity.

The cytokines may be bone morphogenetic protein 2 (BMP2), bone morphogenetic protein 3 (BMP3), platelet derived growth factor (PDGF) (including PDGF-BB and the like), fibroblast growth factor (FGF) (including Basic fibroblast Growth Factor (bFGF) and the like), epidermal growth factor (EGF), transforming growth factor (TGF), vascular endothelial growth factor (VEGF), nerve growth factor (NGF) or neurotrophin3/4(NT3/4), and the like, and their functional subunits, such as β-NGF and the like, preferably BMP2, PDGF-BB, bFGF or β-NGF.

In addition, for convenient purification, the amino terminus of the recombinant fused cytokines may be further linked to a histidine-affinity tag sequence consisting of 6 histidine residues.

Among others, the fused active restoration factors, obtained by fusing a CBD to the N-terminus of BMP2, may have the amino acid sequence of SEQ ID NO: 2 in the Sequence Listing. SEQ ID NO:2 in the Sequence Listing consists of 157 amino acid residues, wherein the amino acid residues at positions 5-10 from the amino terminus are a histidine-affinity tag sequence; the amino acid residues at positions 22-28 from the amino terminus are the conserved sequence of collagen binding domain (CBD); the amino acid residues at positions 44-157 from the amino terminus are BMP2; and the amino acid residues at positions 29-43 from the amino terminus are a linker peptide sequence.

DNA sequence encoding the above fused active restoration factors obtained by fusing a CBD to N-terminus of BMP2, may be SEQ ID NO:3 in the Sequence Listing. SEQ ID NO:3 in the Sequence Listing consists of 477 bases, wherein the bases at positions 13-30 from the 5' end encode a histidine-affinity tag sequence; the bases at positions 64-84 from the 5' end encode the conserved sequence of collagen binding domain; the bases at positions 130-471 from the 5' end encode BMP2; and the bases at positions 85-129 from the 5' end encode a linker peptide sequence.

The fused active restoration factors, obtained by fusing a CBD to the N-terminus of β-NGF, may have the amino acid sequence of SEQ ID NO: 4 in the Sequence Listing. SEQ ID NO:4 in the Sequence Listing consists of 159 amino acid residues, wherein the amino acid residues 5-10 from the amino terminus are a histidine-affinity tag sequence; the amino acid residues 22-28 from the amino terminus are the conserved sequence of collagen binding domain; the amino acid residues 42-159 from the amino terminus are β-NGF; and the amino acid residues 29-41 from the amino terminus are a linker peptide sequence.

DNA sequence encoding the above fused active restoration factors obtained by fusing a CBD to N-terminus of β-NGF, may be SEQ ID NO:5 in the Sequence Listing. SEQ ID NO:5 in the Sequence Listing consists of 480 bases, wherein the bases 16-33 from the 5' end encode a histidine-affinity tag sequence; the bases 67-87 from the 5' end encode the conserved sequence of collagen binding domain; the bases 127-480 from the 5' end encode β-NGF; and the bases 88-126 from the 5' end encode a linker peptide sequence.

The fused active restoration factors, obtained by fusing a CBD to the N-terminus of PDGF-BB, may have the amino acid sequence of SEQ ID NO: 8 in the Sequence Listing. SEQ ID NO:8 in the Sequence Listing consists of 150 amino acid residues, wherein the amino acid residues 5-10 from the amino terminus are a histidine-affinity tag sequence; the amino acid residues 22-28 from the amino terminus are the conserved sequence of collagen binding domain; the amino acid residues 42-150 from the amino terminus are PDGF-BB; and the amino acid residues 29-41 from the amino terminus are a linker peptide sequence.

DNA sequence encoding the above fused active restoration factors obtained by fusing a CBD to N-terminus of PDGF-BB, may be SEQ ID NO:9 in the Sequence Listing. SEQ ID NO:9 in the Sequence Listing consists of 453 bases, wherein the bases 13-30 from the 5' end encode a histidine-affinity tag sequence; the bases 64-84 from the 5' end encode the conserved sequence of collagen binding domain; the bases 124-

450 from the 5' end encode PDGF-BB; and the bases 85-123 from the 5' end encode a linker peptide sequence.

The fused active restoration factors, obtained by fusing a CBD to the N-terminus of bFGF, may have the amino acid sequence of SEQ ID NO: 12 in the Sequence Listing. SEQ ID NO:12 in the Sequence Listing consists of 197 amino acid residues, wherein the amino acid residues 5-10 from the amino terminus are a histidine-affinity tag sequence; the amino acid residues 22-28 from the amino terminus are the conserved sequence of collagen binding domain; the amino acid residues 44-197 from the amino terminus are bFGF; and the amino acid residues 31-41 from the amino terminus are a linker peptide sequence.

DNA sequence encoding the above fused active restoration factors obtained by fusing a CBD to N-terminus of bFGF, may be SEQ ID NO:13 in the Sequence Listing. SEQ ID NO:13 in the Sequence Listing consists of 591 bases, wherein the bases 13-30 from the 5' end encode a histidine-affinity tag sequence; the bases 64-84 from the 5' end encode the conserved sequence of collagen binding domain; the bases 130-591 from the 5' end encode bFGF; and the bases 91-123 from the 5' end encode a linker peptide sequence.

Another object of the present invention is to provide a method for expressing the above mentioned fused active restoration factors.

The expression method of the fused active restoration factor provided by the present invention comprises constructing a recombinant expression vector containing the gene of the fused active restoration factor, transforming a host cell with the constructed recombinant expression vector, culturing the host cell to express the gene of the fused active restoration factor, and obtaining the fused active restoration factor.

The initial vector used to construct the recombinant expression vector may be the expression vector for expressing exogenous gene in *E. coli*, such as pET-28a, pET-28b, pET-28c, pET-21a(+) or pET-30a, preferably pET-28a.

With the pET-28a as an initial vector, the constructed recombinant expression vector containing the gene of the fused active restoration factor is pET-28a-BMP2-h, pET-CBD-NGF, pET-CBD-PDGF or pET-CBD-bFGF, wherein the fused active restoration factor has a binding ability specific for collagen.

The host may be *E. coli*, yeasts, mammalian cells, insect cells, or *Bacillus subtilis*, preferably *E. coli*.

The *E. coli* may be *E. coli* BL21 (DE3), *E. coli* BL21(DE3) plys, *E. coli* BLR (DE3) or *E. coli* B834 and the like.

With *E. coli* BL21(DE3) as an initial strain, the recombinant strain obtained by transforming pET-28a-BMP2-h into *E. coli* BL21(DE3) is BL21(DE3)-pET-28a-BMP2-h; the recombinant strain obtained by transforming pET-CBD-NGF into *E. coli* BL21(DE3) is BL21(DE3)-pET-CBD-NGF; the recombinant strain obtained by transforming pET-CBD-PDGF into *E. coli* BL21(DE3) is BL21(DE3)-pET-CBD-PDGF; and the recombinant strain obtained by transforming pET-CBD-bFGF into *E. coli* BL21(DE3) is BL21(DE3)-pET-CBD-bFGF.

The above recombinant expression vectors and recombinant strains all can be constructed according to conventional approaches.

The media and culture conditions for culturing the host cells containing the gene of the fused active restoration factor of the present invention all can be used as those for culturing initial hosts. Among others, an inducer such as IPTG may be added at a concentration of 0.8-1.2 mmol/L, preferably 1 mmol/L when culturing recombinant *E. coli* host cells, at an induction temperature of 35-39° C. and preferably 37° C. for an induction period of 2-4 hours, preferably 4 hours.

Another object of the present invention is to provide an activated collagen restoration material.

The activated collagen restoration material provided by the present invention is a collagen loaded with the above mentioned fused active restoration factors.

The loading amount of the fused active restoration factors is 1-4000 pmol protein per mg collagen.

The present invention is further illustrated in detail together with the following specific embodiments.

PREFERRED EMBODIMENTS OF THE INVENTION

Figure 1A:
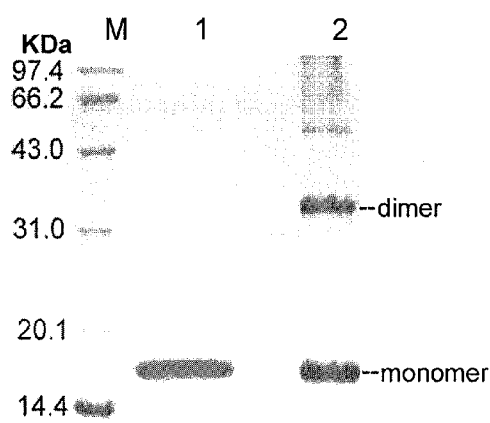
FIG. 1A shows the results of 15% SDS-PAGE of the expressed protein upon purification and renaturation.

The methods used in the following examples are all conventional methods unless otherwise stated.

EXAMPLE 1

Cloning, Expression, Purification and Function Identification of the Gene Encoding the Fused Active Restoration Factors which has the Ability of Specifically Binding to Collagen I. Cloning, Expression and Purification of the Gene Encoding the Fused Active Restoration Factor BMP2, Which has the Ability of Specifically Binding to Collagen 1. Cloning of the Gene Encoding the Fused Active Restoration Factor BMP2, Which has the Ability of Specifically Binding to Collagen and Construction of Its Expression Vector PCR amplification primers were designed according to the known cDNA sequence of human BMP2 (hBMP2) (GenBank Accession No.: 50), and the coding sequence of collagen binding domain (CBD) "TKKTLRT" (SEQ ID NO: 1 in the Sequence Listing) was introduced into the forward primers. The primer sequences are as follow:

```
hBMP2F1 (forward primer):
                                (SEQ ID NO: 16)
5'-TACCGGTAGCGCGGGCAGTGCTGCGGGTTCTG

GCGGTGTCGACCAAGCCAAACAC-3' hBMP2F2 (forward primer):
                                (SEQ ID NO: 17)
5'-CCGCATATGACTAAGAAAACCCTGCGTACTGG

TACCGGTAGC-3' hBMP2R (reverse primer):
                                (SEQ ID NO: 18)
5'-CCGCTCGAGCTATTAACGACAACCACAACC-3'
```

Using full-length human BMP2 cDNA as templates, PCR amplification was performed with primer hBMP2F1 and hBMP2R. The 30 µl PCR reaction system contained: 1 pmol/µl of each of forward and reverse primer, dNTPs 200 µmol/µl, Taq DNA polymerase 3 µl. The PCR reaction condition was: pre-denaturation at 94° C. for 5 min; and then denaturation at 94° C. for 30 s, annealing at 55° C. for 1 mM, extension at 72° C. for 1 min, 30 cycles; final extension at 72° C. for 10 min. At the end of the reaction, the amplification product was analyzed by electrophoresis on 1.5% agarose gel and a DNA fragment of about 400 bp was obtained from the PCR amplification. After recovery and purification, the fragment, as the template of the second round PCR, was used to perform the second round PCR with primer hBMP2F2 and hBMP2R again, and the PCR reaction system and condition were the same as above. After amplification, the PCR product was analyzed by electrophoresis on 1.5% agarose gel, and a band of about 430 kb was obtained. After recovery and purification, the fragment was double digested with restriction endonuclease Ned I and Xho I, and ligated using T4 DNA ligase at 16° C. for 12-24 hours with prokaryotic expression vector pET-28a (Novagen), which was double digested with the same enzymes. The ligation product was transformed into E. coli DH5α competent cells, screening for positive clone, extracting plasmid, sequencing the multiple cloning site region of the expression vector. The inserted sequence matched the anticipated sequence and has the nucleotide sequence of SEQ ID NO: 3 in the Sequence Listing. The SEQ ID NO: 3 in the Sequence Listing is consisted of 477 bases and encodes the amino acid sequence of SEQ ID NO: 2 in the Sequence Listing, which includes CBD region, coding sequences of linking peptide and hBMP2 mature peptide. A histidine-affinity tag sequence, the amino acid residues 5-10 from the amino terminus, was fused in front of the inserted region. The conserved region of the CBD region is amino acid residues 22-28 from the amino terminus of SEQ ID NO: 2. The linking peptide is amino acid residues 29-34 from the amino terminus, the hBMP2 mature peptide is amino acid residues 44-157 from the amino terminus. It was indicated that the correct recombinant plasmid containing the coding sequence of special active restoration factor was obtained and it was named as pET-28a-BMP2-h.

2. Prokaryotic Expression of Special Fused Active Restoration Factors

The prokaryotic expression vector pET-28a-BMP2-h constructed in step 1 was transformed into E. coli BL21(DE3) competent cells and the screened recombinant E. coli containing pET-28a-BMP2-h was named as BL21(DE3)-pET-28a-BMP2-h. Positive single colonies were picked up, inoculated in LB broth, and cultured at 37° C. for 12-24 hrs. They were inoculated at 2% into 100 mL LB broth, and cultured at 37° C. for 3 hrs until $OD_{600}$ reached 0.8. IPTG was added at the final concentration of 1 mM, and they were cultured with induction under the same condition for another 4 hrs. After culturing, thallus was collected by centrifugation, washed with PBS, and collected by centrifugation again. The collected thallus was resuspended in 10 mL PBS, supersonicated and the lysate was examined using 15% SDS-PAGE. The result indicated that the crude extract of protein was obtained and the expressed protein was present in the form of inclusion body.

3. Purification and Renaturation of Special Fused Restoration Factors

Firstly, the inclusion bodies were collected from the supersonicated thallus of step 2. Ultrafiltration and concentration were performed on the protein solution obtained by diluting-renaturation, then the protein solution system was exchanged with 50 mM MES buffer (commercially available from GIBCO), and cryopreserved after lyophilization. After purification and renaturation, the expressed protein was analyzed on 15% SDS-PAGE and the result is shown in FIG. 1A (lane M is marker, lane 1 is the expressed protein after purification (under reducing condition), lane 2 is the expressed protein after renaturation). The purification result in lane 1 indicates that the target protein of 15 KD is considerably pure. Because the active form of BMP2 is dimer formed through a pair of disulfate bond, a band corresponding to the dimer can be visualized under non-reducing condition. The examination result in lane 2 indicates that the dimer formed by renaturation has reached to 30%. The purified special fused active restoration factor is named as rhBMP2-h.

Figure 1B:
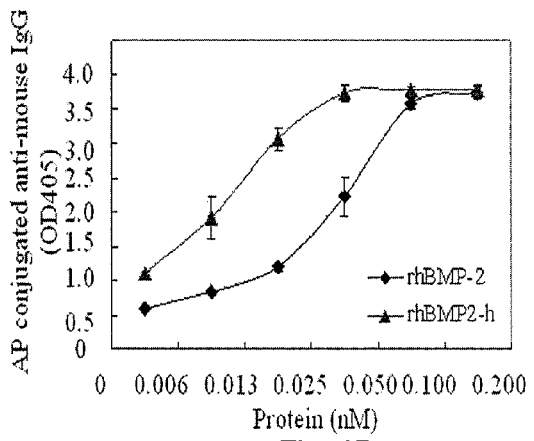
FIG. 1B shows the statistic results for the type I collagen-binding capacity of natural BMP2 and special fused active restoration factor rhBMP2-h with a gradually increasing concentration.

II. Determination of Special Fused Active Restoration Factors for Activity to Bind to Collagen 1. Collagen Binding Capacity Analysis of Special Fused Active Restoration Factors 1) Determination of the Binding Capacity of Equal Amount of Collagen to Different Amounts of Natural BMP2 and Special Fused Active Restoration Factor The natural BMP2 and special fused active restoration factors prepared in step I of gradually increasing concentration were loaded onto a collagen membrane prepared with equal amount of type I collagen. After full absorption, the non-binding protein was washing off with PBS, the protein binding capacity was determined by measuring the specific quantitativable color reaction generated by the antibody binding to the fused tag, and the statistical result is shown in FIG. 1B (the horizontal coordinates is the loading amount of protein, and the vertical coordinates is the absorbance at 405 nm). After the protein concentration reaches certain threshold, the binding capacity of collagen to protein all can reaches the same saturation capacity. However, before reaching the threshold, under the condition of the same protein loading amount, the remaining amount of re-constructed rhBMP2-h is significantly higher than that of natural BMP2 (rhBMP2), i.e. the binding efficiency of the former is significantly higher than that of the latter. The result indicates that the binding capacity of re-constructed BMP2 to collagen is enhanced dramatically compared to natural BMP2.

Figure 1C:
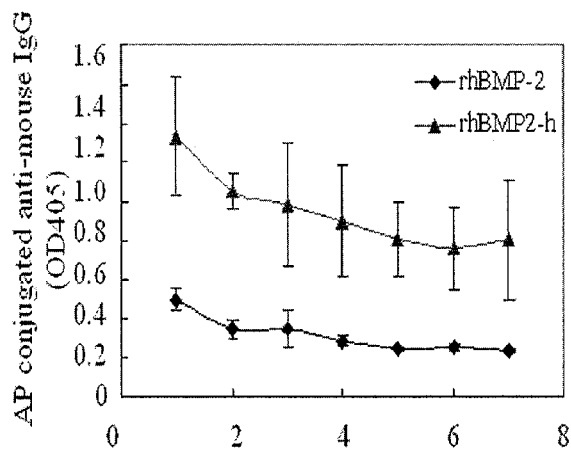
FIG. 1C shows the results for the type I collagen-binding ability of equal amount of natural BMP2 and special fused active restoration factor rhBMP2-h.

2) Determination of Equal Amount of Natural BMP2 and Special Fused Active Restoration Factor for the Binding Ability to Type I Collagen Equal amount of natural BMP2 and special fused active restoration factors prepared in step I were loaded onto the collagen membrane made from type I collagen. After fully absorbed, they were eluted with various concentrations of urea, respectively. The protein binding capacity can be determined by measuring the specific quantitativable color reaction caused by the antibody binding to the fused tag. The statistical result of protein binding capacity is shown in FIG. 1C (the horizontal coordinates is the urea concentration, and the vertical coordinates is the absorbance at 405 nm). The binding curve of re-constructed rhBMP2-h to collagen is significantly higher than that of natural BMP2, and under the level of low urea concentration, the remaining amount of natural BMP2 on collagen decreased dramatically, rapidly approaching its base level.

The above-mentioned experiments proved the specific binding ability of BMP2 to collagen from different views, indicating the binding ability of re-constructed special fused active restoration factor rhBMP2-h to collagen was increased significantly.

III. Cell Activity Test on Special Fused Active Restoration Factors

Figure 1D:
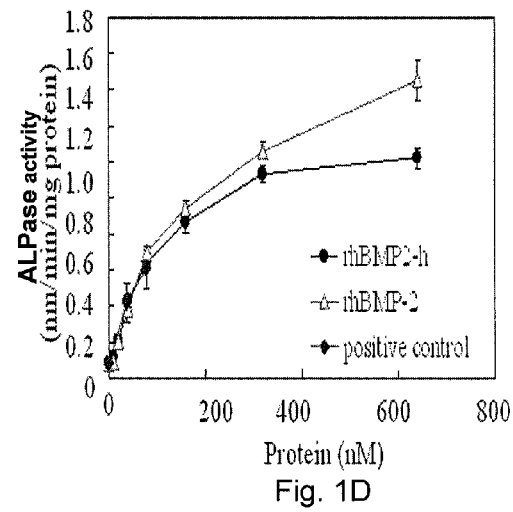
FIG. 1D shows the test results for the cell activities of special fused active restoration factor rhBMP2-h.

The major effect of BMP2 on cells is promote cells to differentiate to osteoblast. By culturing somatocytes, Hiraki has discovered that BMP2 has strong stimulating effect on osteoblastic cell MC3T3-E1, and the ALPase (alkaline phosphatase) activity of this kind of cell can be increased 5-20 fold by 100 ng/mL BMP2 (Hiraki, Y. et al. Bone morphogenetic proteins (BMP2 and BMP-3) promote growth and expression of the differentiated phenotype of rabbit chondrocytes and osteoblastic MC3T3-E1 cells in vitro. J. Bone Miner Res. 6, 1373-85 (1991)). Furthermore, BMP2 has strong transdifferentiation effect on sarcoblast C2C12, preventing it from differentiating to muscle cells, but to osteoblast. Mouse sarcoblast cell line C2C12 (purchased from the cell bank of the Basic Medical Institute of Peking Union Medical College) was used to test the in vitro activity of the special fused active restoration factors prepared in step I. The method includes: stimulating C2C12 cells with different concentrations of rhBMP2-h, testing the activity of ALPase after 3-day stimulation. The positive control group used the rhBMP2 (commercially available from Sigma) secreted by CHO cell, the experimental control group used natural BMP2 without the collagen binding domain (rhBMP2). The testing result is shown in FIG. 1D (the horizontal coordinates is the protein concentration, and the vertical coordinates is the ALPase activity). The ALPase activity increases as the concentration of rhBMP2-h increases, showing the dose-dependent effect; and through statistical analysis, each experimental group has significant difference from the control group (P<0.05). The above results indicate the diluting-renatured special fused active restoration factors have higher biological activity.

IV. Animal Experiment—Ectopic Osteoinduction

The classical method of ectopic bone formation was often employed to test the bone induction activity of BMP2 in vitro, i.e. the BMP2 was transplanted into ectopic tissues other than bone tissues, histological slice and X-ray imaging were used at different intervals after implantation to observe its bone induction activity in the tissue (Wozney, J. M., et al, Novel regulators of bone formation: molecular clones and activities. Science 242, 1528-34 (1988); Urist, M. R. Bone: formation by autoinduction. 1965. Clin. Orthop. Relat. Res, 4-10 (2002)).

The same method as above was employed in this experiment to determine the activities of natural BMP2 and the special fused active restoration factor prepared in step I, the detailed experimental method and result are described as follow:

The experiment was divided into three groups: natural BMP2 (rhBMP2) group, special fused active restoration factor rhBMP2-h group, and the control group. Firstly, collagen (from bovine tendon) was cut into 1 cm×1 cm×0.1 cm square slices, and 30 pmol protein was loaded onto each milligram collagen, and only PBS was loaded for control group. They were lyophilized for future use.

Figure 1E:
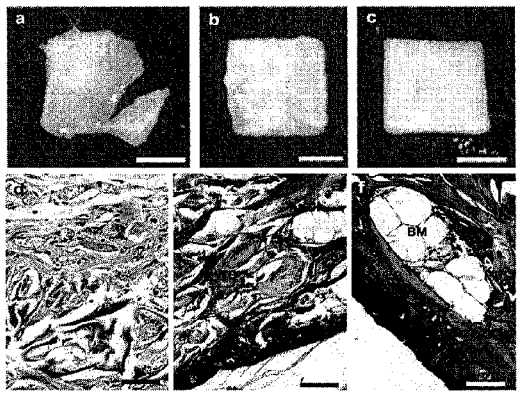
FIG. 1E shows the results for the ectopic osteoinduction experiments of natural BMP2 and special fused active restoration factor rhBMP2-h.

Male adult SD rats were selected and the collagen slices loaded with different proteins above were embedded under the skin on their back. After 4-week embedment, the embedded materials were taken out, sliced and HE stained. The result is shown in FIG. 1E (scale bars in panels a, b, c represents 5 mm; scale bars in panels d, e, f represents 30 µm). The panels a and d in FIG. 1E represent respectively the observing result of the collagen slices transplanted and histological slices in the control group without being loaded with any protein. Since the prepared collagen scaffold material has good biodegradability, it can be seen that the embedded material has been partially degraded, the scaffold has become thinner and softer in entirety, and its edge has become uneven. The result of histological slices did not show any signs of bone formation. Panels b and e show respectively the observing result of the collagen slices transplanted and histological slices in the experimental group being loaded with natural BMP2. As rhBMP2 itself has the ability of ectopic bone induction, loading it onto collagen inhibited the diffusion of rhBMP2 to some extent through collagen structure, initiated the process of bone formation to some extent, induced a few of mesenchymal cells to differentiate to bone cells, and thus secreted small amount of collagen matrix and calcium ions deposited onto the material. The apparent exhibition is that the embedded material is thicker than the negative control group, its degradation rate also gets slower and its histological slices shows the formation of small amount of woven bones (WB). Panels c and f represent respectively the observing result of the collagen slices transplanted and histological slices in the experimental group being loaded with the special fused active restoration factor rhBMP2-h. The re-constructed rhBMP2-h has relatively strong specific binding ability to collagen. It is no easy to diffuse and to be diluted after implantation, and always keeps relatively high concentration at the effective site, inducing large amount of mesenchymal cells to differentiate to bone cells. The differentiated bone cells then secrete large amount of new collagen matrix and calcium ion deposited onto the existing collagen material. A part of rhBMP2-h released by degradation of the existing collagen material may bind to newly formed collagen. The apparent exhibition is that the degradation rate of the collagen material slices gets slower, the size change is not significant, and the material gets harder due to the deposition of large amount of calcium ion. The histological slices show the formation of lamella bones (LB), and the formation of bone marrows can be seen as well. The above experiment results indicate the ectopic osteoinduction effect of the activated collagen material loaded with the special fused active restoration factor of the present invention is dramatically superior to the control group.

EXAMPLE 2

Cloning, Expression, Purification and Function Identification of the Gene Encoding the Fused Active Restoration Factors β-NGF which has the Ability of Specifically Binding to Collagen I. Cloning, Expression and Purification of the Gene Encoding the Fused Active Restoration Factor β-NGF, Which has the Ability of Specifically Binding to Collagen
1. Cloning of the Gene Encoding the Fused Active Restoration Factor β-NGF, Which has the Ability of Specifically Binding to Collagen and Construction of Its Expression Vector
 1) Primer Design
 Three forward primers (CBDU, NGFU1, and NGFU2, referring to Table 1 for their sequences) and two reverse primers (CBDD and NGFD, referring to Table 1 for their sequences) were designed using Primer premier 5.05 software, wherein CBDU (introducing a recognition site of restriction endonuclease NdeI) and CBDD (introducing a recognition site of restriction endonuclease HindIII) were used to amplify the coding sequences of collagen binding domain and the linking peptide (LINKER), wherein the conserved amino acid sequence of CBD is TKKTLRT (SEQ ID NO:1 in the Sequence Listing) and the amino acid sequence of the linking peptide is GSAGSAAGSGGK (SEQ ID NO: 24); NGFU1 (introducing a recognition site of restriction endonuclease NdeI) and NGFD (introducing a stop codon and a recognition site of restriction endonuclease Xho I) were used to amplify the coding sequence of β-NGF; NGFU2 (introducing a recognition site of restriction endonuclease HindIII) and NGFD (introducing a stop codon and a recognition site of restriction endonuclease Xho I) were also used to amplify the coding sequence of β-NGF.

TABLE 1

Primer Sequences

CBDU:
(SEQ ID NO: 19)
5'-ATCCATATGACTAAGAAAACCCTGCGTACTGGTAGCGCGGGCAGT-3'
(the underlined bases is the recognition site of restriction endonuclease Nde I)

CBDD:
(SEQ ID NO: 20)
5'-ACTAAGCTTACCGCCAGAACCCGCAGCACTGCCCGCGCTACCAGT-3'
(the underlined bases is the recognition site of restriction endonuclease Hind III)

NGFU1:
(SEQ ID NO: 21)
5'-CTACATATGTCTTCGTCCCATCCCATCTTCCAC-3'
(the underlined bases is the recognition site of restriction endonuclease Nde I)

NGFU2:
(SEQ ID NO: 22)
5'-GCTAAGCTTTCTTCGTCCCATCCCATCTTCCAC-3'
(the underlined bases is the recognition site of restrictionendonuclease Hind III)

NGFD:
(SEQ ID NO: 23)
5'-GATCTCGAGTCATCTCACAGCCTTCCTGCTGAGCAC-3'
(the underlined bases is the recognition site of restriction endonuclease Xho I)

2) The PCR Amplification of the Coding Sequence of the Fused Active Restoration Factor β-NGF Having the Ability of Specifically Binding to Collagen, and the Construction of Its Expression Vector
 CBDU and CBDD were used mutually as templates, the coding sequences of CBD and the linking peptide were amplified by the overlap extension PCR, wherein 50 μl PCR reaction system was: 1 pmol/μl of each of primer CBDU and CBDD, 200 pmol/μl dNTPs, 1 μl Taq polymerase, adding ddH₂O to 50 μl. The PCR reaction condition was: predenaturation at 94° C. for 5 min; then denaturation at 94° C. for 30 sec, annealing at 55° C. for 1 min, extension at 72° C. for 1 min, 30 cycles; final extension at 72° C. for 10 min. At the end of the reaction, the PCR amplification product was analyzed by electrophoresis on 1.5% agarose gel, which resulted into a band about 70 bp. After the target band was recovered and purified, it was double digested with restriction endonucleases Nde I and Hind III and then ligated to the prokaryotic expression vector pET28a (Novagen) which was double digested with the same endonucleases. The recombinant was sequenced and the result indicated that the coding sequences of CBD and the linking peptide with correct sequence were obtained. The recombinant vector ligated correctly with the sequence was named as pET-CBD.
 By using the full length cDNA of human β-NGF gene (GenBank Assession No. NM 002506) as the template, human β-NGF gene was amplified with the primer pairs of NGFU1 and NGFD, as well as NGFU2 and NGFD, respectively. The 50 μl PCR reaction system was: 1 pmol/μl of upstream and downstream primers respectively, 200 μmol/μl dNTPs, 1 μl Taq polymerase, adding ddH₂O to 50 μl. The PCR reaction condition was: predenaturation at 94° C. for 5 min; denaturation at 94° C. for 45 s, annealing at 55° C. for 1 min, extension at 72° C. for 1 min, 30 cycles; finally 72° C. for 10 min for adequate extension. At the end of the reaction, the PCR product was analyzed by electrophoresis on 1.5% agarose gel, which resulted into two bands about 350 bp. After the two target bands were recovered and purified, the amplified product of BGFU1 and NGFD primers was double digested with Nde I and Xho I and ligated to the prokaryotic expression vector pET28a which was double digested with the same endonucleases. The recombinant vector was and the result indicates that the correct coding sequence of β-NGF mature peptide with the histidine-affinity tag was obtained. It has the nucleotide sequence of SEQ ID NO:7 in the Sequence Listing, which is consisted of 420 bases, encoding the amino acid sequence of SEQ ID NO:6 in the Sequence Listing, which is consisted of 139 amino acid residues. The recombinant vector ligated correctly with the sequence was named as pET-NAT-NGF. Meanwhile, the amplification band of BGFU2 and NGFD primers was double digested with endonucleases Hind III and Xho I, and ligated to the prokaryotic expression vector pET-CBD which was double digested with the same endonucleases. The recombinant was sequenced and the result indicated that the correct coding sequence of the fusion protein comprising histidine-affinity tagged CBD and β-NGF mature peptide was obtained. The said sequence has the nucleotide sequence of SEQ ID NO:5 in the Sequence Listing, which is consisted of 480 bases. The bases 16-33 from the 5'-end of the sequence encode the sequence of histidine-affinity tag; the bases 67-87 from the 5'-end of the sequence encode the conserved sequence of collagen binding domain; the bases 127-480 from the 5'-end of the sequence encode β-NGF; the bases 88-126 from the 5'-end of the sequence encode the sequence of the linking peptide. The SEQ ID NO:5 in the Sequence Listing encodes the amino acid sequence of SEQ ID NO:4 in the Sequence Listing, which is consisted of 159 amino acid residues. The recombinant vector ligated correctly the sequence was named as pET-CBD-NGF.

Figure 1F:
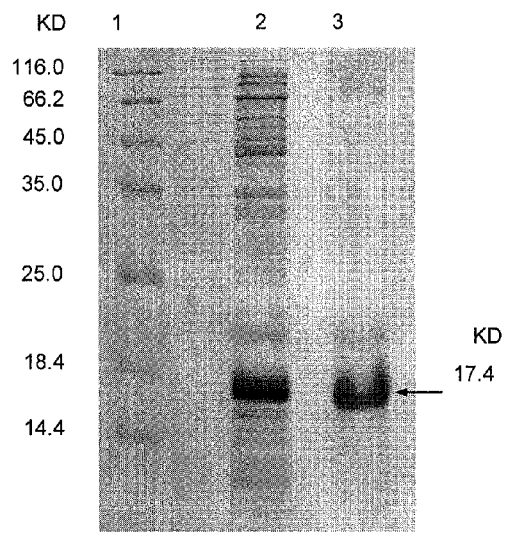
FIG. 1F shows the SDS-PAGE results for histidine-affinity tagged fusion protein comprising a collagen binding domain and a β-NGF mature peptide, upon expression and purification.

2. Expression and Purification of the Fused Active Restoration Factor β-NGF with the Ability of Specifically Binding to Collagen The prokaryotic expression vector pET-NAT-NGF having the coding sequence of β-NGF mature peptide with the histidine-affinity tag and the prokaryotic expression vector pET-CBD-NGF having the coding sequence of the histidine-affinity tagged fusion protein comprising the collagen binding domain and the β-NGF mature peptide, which were constructed in step 1, were used to transform $E.$ $coli$ BL21 (DE3) competent cells. The transformed cells were spread on the LB plates and cultured at 37° C. Single colonies were picked up, inoculated into LB broth, and cultured at 37° C. for 12-24 hours. They were inoculated at 2% ratio into 100 mL LB broth and cultured at 37° C. for 3 hours, until the $OD_{600}$ reached about 0.8. IPTG at the final concentration of 1 mM were added and they were cultured for another 4 hours. After culturing, thallus was harvested by 8000 rpm centrifugation, washed with PBS (NaCl 8.5 g, $Na_2HPO_4$ 2.2 g, $NaH_2PO_4$ 0.4 g dissolved in 100 mL dd$H_2O$, pH7.2), and harvested again by centrifugation after wash. The thallus was resuspended in 10 mL PBS and supersonicated, which resulted into the crude extract of the recombinant protein. The inclusion bodies were collected by centrifugation and purified using the affinity chromatographic column of fixed metal ion ($Ni^{2+}$) ligand (Amersham biosciences) after washing and dissolving. The two purified expression products were renatured by dialysis, and concentrated by ultra-filtration. The protein solution system was exchanged with citrate buffer (citric acid 0.4 g, sodium citrate 2.38 g, dissolved in 100 mL dd$H_2O$, pH6.0), and kept at 4° C. The expression and purification product of pET-CBD-NGF was analyzed on 15% SDS-PAGE, and the result is shown in FIG. 1F, in which lane 1 is the standard of protein molecular weight; lane 2 is the expression thallus after sonication; and lane 3 is the inclusion bodies after purification (under reducing condition). The recombinant protein with the molecular weight of about 15.4 Kd was obtained by expression, which matched the expected result. As can be seen from the figure, the target protein is mainly expressed in the form of inclusion body. After purification, relatively high purity of nerve growth factor with the ability of specifically binding to collagen was obtained, i.e. the histidine-affinity tagged fusion protein comprising the collagen binding domain and β-NGF mature peptide, which was named as CBD-NGF. The recombinant $E.$ $coli$ expressing this protein was named as BL21 (DE3)-pET-CBD-NGF. And the β-NGF mature peptide with the histidine-affinity tag was named as NAT-NGF.

Figure 2A:
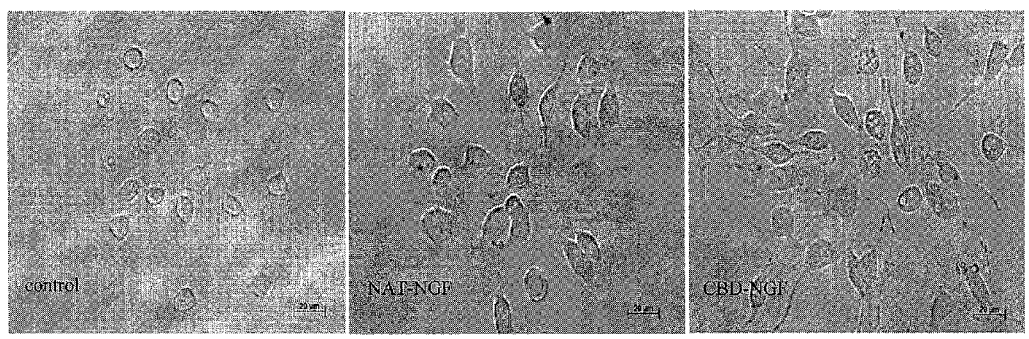
FIG. 2A shows the morphological observation of PC12 cells upon CBD-NGF and NAT-NGF induction.
Figure 2B:
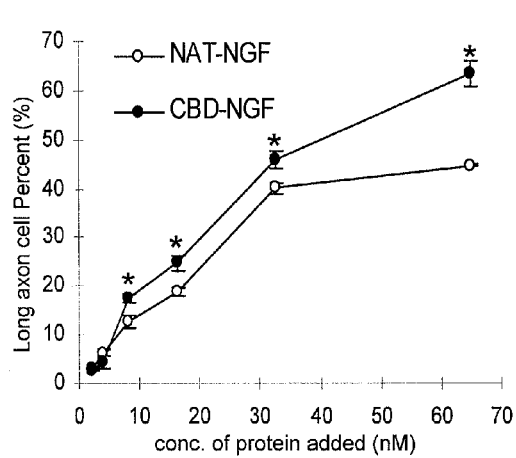
FIG. 2B shows the results for the axon induction experiment of PC12 cells upon CBD-NGF and NAT-NGF induction.
Figure 2C:
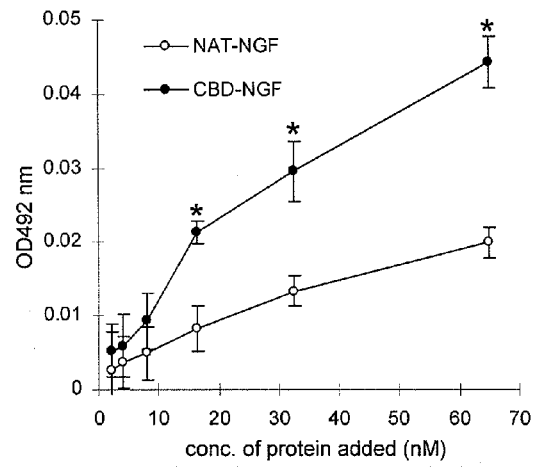
FIG. 2C shows the results for MTT experiment of PC12 cells after CBD-NGF and NAT-NGF induction.

II. Activity Test of the Fused Active Restoration Factor β-NGF with the Ability of Specifically Binding to Collagen Rat adrenal chromaffin cells PC12 can differentiate to axons by NGF induction. In addition, NGF can promote the survival of neurons. Therefore, the activities of CBD-NGF and NAT-NGF obtained in step I were tested by PC12 (commercially available from the cell bank of the Basic Medical Institute of Peking Union Medical College) axon induction experiment and MTT experiment (Howe, C. L., *Depolarization of PC12 cells induces neurite outgrowth and enhances nerve growth factor-induced neurite outgrowth in rats*. Neurosci Lett, 2003. 351(1):p. 41-5). The method of the test was: the PC12 cells were stimulated with CBD-NGF and NAT-NGF of the concentration of 0-64 nM, and the non-stimulated PC12 cells were taken as a control. After one day stimulation, PC12 cells had the induced axon generation (FIG. 2A). The ratio of the cell with long axon was calculated, and the statistical result is shown in FIG. 2B. As can be seen, the ratio of cells with long axon increased with the increase of CBD-NGF concentration, showing the dose-dependent effect. The statistical analysis revealed that there is significant difference between β-NGF with the CBD (CBD-NGF) and β-NGF without the CBD (NAT-NGF) (*: $p<0.05$; **: $p<0.01$). Moreover, MTT experiment was performed after 3-day treatment with β-NGF and the result is shown in FIG. 2C. Similarly, the $OD_{492}$ increased as the β-NGF concentration increased, indicating the number of survival cell increased. The results of the above experiments all showed dose-dependent effect and the statistical analysis revealed that there is significant difference between the experiment results of the two proteins (*: $p<0.05$; **: $p<0.01$). The result indicates that the dialysis renatured proteins CBD-NGF and NAT-NGF both have biological activity, and the activity of CBD-NGF is significantly higher than that of NAT-NGF.

III. Test of the Binding Ability of CBD-NGF to Collagen

Figure 3A:
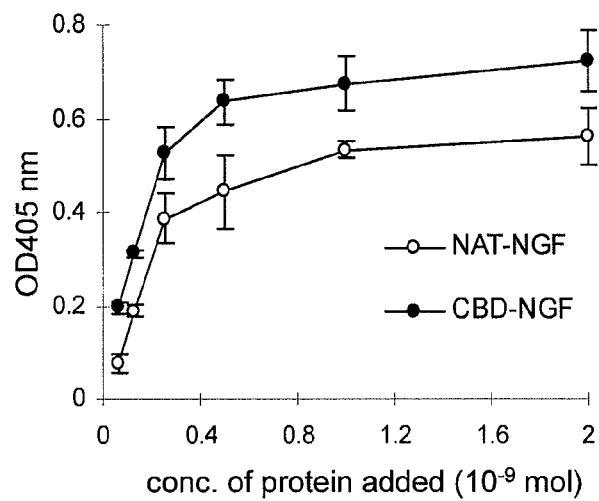
FIG. 3A shows the test results for the binding capacity of equal amount of collagen to different amounts of NAT-NGF and CBD-NGF.
Figure 3B:
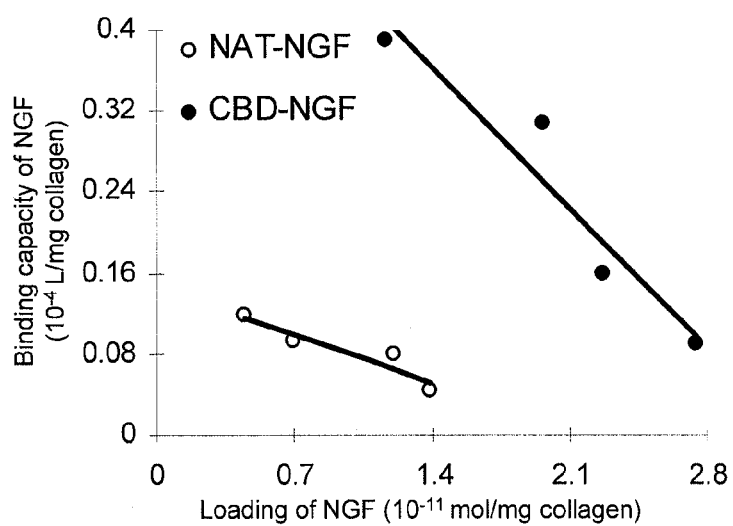
FIG. 3B shows the calculation results for the dissociation constant Kd of NAT-NGF and CBD-NGF against collagen.

The aim of preparing CBD-NGF by genetic engineering technique and microorganism fermentation is to maintain its activity and meanwhile enhance its binding ability to collagen 3-D scaffold material used in tissue engineering, in order to reduce the effective amount of β-NGF. Improved ELISA experiment was used to determine the ability of NAT-NGF and CBD-NGF to bind to collagen membrane respectively (Finnis, M. L. and M. A. Gibson, *Microfibril-associated glycoprotein-1 (MAGP-1) binds to the pepsin-resistant domain of the alpha3(VI) chain of type VI collagen*. J Biol Chem, 1997. 272(36): p. 22817-23), and the dissociation constants of the two proteins against collagen Kd were calculated according to Matsushita's method (Matsushita, O., et al., *A study of the collagen-binding domain of a 116-kDa Clostridium histolyticum collagenase*. J Biol Chem, 1998. 273(6): p. 3643-8). The gradually increasing dose of NAT-NGF and CBD-NGF were loaded onto the collagen membrane (6.0 mg) made of equal amount of type I collagen. After full absorption, the non-binding protein was washed off with PBS, and the test result of the binding capacity of equal amount of collagen (6.0 mg) to various amounts of NAT-NGF and CBD-NGF is shown in FIG. 3A. Under the condition of same loading quantity of protein, the remaining amount of CBD-NGF on the collagen membrane is dramatically higher than that of NAT-NGF, indicating that the binding efficiency of the former is significantly higher than that of the latter. Furthermore, the dissociation constants Kd of NAT-NGF and CBD-NGF are 1.50 µM and 0.51 µM respectively (FIG. 3B). According to the definition of Kd, the lower the Kd of a protein, the stronger its ability of binding to collagen. The results of the experiments above indicate that the ability of CBD-NGF to bind to collagen is increased dramatically compared to NAT-NGF.

IV. The In Vitro Function Assay of CBD-NGF

Figure 4:
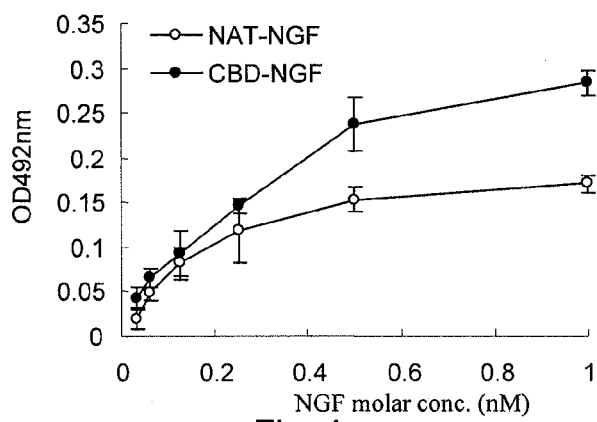
FIG. 4 shows the results of in vitro function assay for NAT-NGF and CBD-NGF.

Firstly, the gradually increasing concentration of NAT-NGF and CBD-NGF were loaded onto the 48-well plate which was coated (0.2 mg collagen/well) by acidic collagen (from mouse tail). After absorption for 1 hour, wash twice with PBS, and PC12 cells were then inoculated in the 48-well plate, 5×10³ cells each well, and cultured at 37° C. for 3 days. The number of survival cell was then determined by MTT method and the result is shown in FIG. 4. Compared to NAT-NGF, CBD-NGF has higher activity on the collagen, and can promote the survival and growth of PC12 cells better, and can be used clinically for the restoration of nerve injury.

EXAMPLE 3

Cloning, Expression, Purification and Function Identification of the Gene Encoding the Fused Active Restoration Factor PDGF-BB (Platelet-Derived Growth Factor) Which has the Ability of Specific Binding to Collagen I. Cloning, Expression and Purification of the Gene Encoding the Fused Active Restoration Factor PDGF-BB, Which has the Ability of Specifically Binding to Collagen
1. Cloning of the Gene Encoding the Fused Active Restoration Factor PDGF-BB, Which has the Ability of Specifically Binding to Collagen and Construction of Its Expression Vector
1) Primer Design Three forward primers (CBDU, PDGFU11, and PDGFU21, referring to Table 2 for their sequences) and two reverse primers (CBDD and PDGFD1, referring to Table 2 for their sequences) were designed using Primer premier 5.05 software as an assistance, wherein CBDU (introducing a recognition site of restriction endonuclease NdeI) and CBDD (introducing a recognition site of restriction endonuclease HindIII) were used to amplify the coding sequences of collagen binding domain and the linking peptide (LINKER), wherein the conserved amino acid sequence of CBD is TKKTLRT (SEQ ID NO:1 in the Sequence Listing) and the amino acid sequence of the linking peptide is GSAGSAAGSGGK (SEQ ID NO: 24); PDGFU11 (introducing a recognition site of restriction endonuclease NdeI) and PDGFD1 (introducing a stop codon and a recognition site of restriction endonuclease Xho I) were used to amplify the coding sequence of PDGF-BB; PDGFU21 (introducing a recognition site of restriction endonuclease HindIII) and PDGFD1 (introducing a stop codon and a recognition site of restriction endonuclease Xho I) were also used to amplify the coding sequence of PDGF-BB.

TABLE 2

Primer Sequences

CBDU:
(SEQ ID NO: 19)
5'-ATCCATATGACTAAGAAAACCCTGCGTACTGGTAGCGCGGGCAGT-3'
(the underlined bases is the recognition site of restriction endonuclease Nde I)

CBDD:
(SEQ ID NO: 20)
5'-ACTAAGCTTACCGCCAGAACCCGCAGCACTGCCCGCGCTACCAGT-3'
(the underlined bases is the recognition site of restriction endonuclease Hind III)

PDGFU11:
(SEQ ID NO: 25)
5'-CTACATATGAGCCTGGGTTCCCTGACCATTG-3'
(the underlined bases is the recognition site of restriction endonuclease Nde I)

PDGFU21:
(SEQ ID NO: 26)
5'-GCTAAGCTTAGCCTGGGTTCCCTGACCATTG-3'
(the underlined bases is the recognition site of restriction endonuclease Hind III)

PDGFD1:
(SEQ ID NO: 27)
5'-GATCTCGAGTCAGGTCACAGGCCGTGCAGCTGCC-3'
(the underlined bases is the recognition site of restriction endonuclease Xho I)

2) The PCR Amplification of the Coding Sequence of the Fused Active Restoration Factor PDGF-BB with the Ability of Specifically Binding to Collagen, and the Construction of Its Expression Vector CBDU and CBDD were used mutually as templates, the coding sequences of CBD and the linking peptide were amplified by the overlap extension PCR, wherein 50 µl PCR reaction system was: 1 pmol/µl of each of primer CBDU and CBDD, 200 µmol/µl dNTPs, 1 µl Taq polymerase, adding ddH₂O to 50 µl. The PCR reaction condition was: predenaturation at 94° C. for 5 min; then denaturation at 94° C. for 30 sec, annealing at 55° C. for 1 min, extension at 72° C. for 1 min, 30 cycles; final extension at 72° C. for 10 min. At the end of the reaction, the PCR amplification product was analyzed by electrophoresis on 1.5% agarose gel, which resulted into a band about 70 bp. After the target band was recovered and purified, it was double digested with restriction endonucleases Nde I and Hind III and then ligated with the prokaryotic expression vector pET28a (Novagen co.) which was double digested with the same endonucleases. The recombinant vector was sequenced and the result indicated that correct coding sequences of CBD and the linking peptide were obtained. The recombinant vector ligated correctly with the sequence was named as pET-CBD.

Using the full length cDNA (GenBank Assession No. CU013426) of PDGF-BB gene as template, PDGF-BB gene was amplified with the primer pairs of PDGFU11 and PDGFD1, as well as PDGFU21 and PDGFD1 respectively. The 50 µl PCR reaction system was: 1 pmol/µl of each of upstream and downstream primers, 200 µmol/µl dNTPs, 1 µl Taq polymerase, adding ddH₂O to 50 µl. The PCR reaction condition was: predenaturation at 94° C. for 5 min; denaturation at 94° C. for 45 s, annealing at 55° C. for 1 min, extension at 72° C. for 1 min, 30 cycles; finally 72° C. for 10 min for adequate extension. At the end of the reaction, the PCR amplification product was analyzed by electrophoresis on 1.5% agarose gel, which resulted into two bands about 340 bp. After the two target bands were recovered and purified, the amplification bands of PDGFU11 and PDGFD1 primers were double digested with Nde I and Xho I and ligated with the prokaryotic expression vector pET28a which was double digested with the same endonucleases. The recombinant vector was sequenced and the result indicates that the correct coding sequence of PDGF-BB mature peptide with the histidine-affinity tag was obtained. It has the nucleotide sequence of SEQ ID NO:11 in the Sequence Listing, which is consisted of 393 nucleotides, encoding the amino acid sequence of SEQ ID NO:10 in the Sequence Listing, which is consisted of 130 amino acid residues. The recombinant vector ligated correctly with the sequence was named as pET-NAT-PDGF. Meanwhile the amplification bands of PDGFU21 and PDGFD1 primers were double digested with Hind III and Xho I, and ligated with the prokaryotic expression vector pET-CBD which was double digested with the same endonucleases. The recombinant vector was sequenced and the result indicated that the correct coding sequence of the fusion protein comprising histidine-affinity tagged CBD and PDGF-BB mature peptide. The said sequence has the nucleotide sequence of SEQ ID NO:9 in the Sequence Listing, which is consisted of 453 bases. The bases 13-30 from the 5'-end of the sequence encode the sequence of histidine-affinity tag; the 64-84 bases from the 5'-end of the sequence encode the conserved sequence of collagen binding domain; the bases 124-450 from the 5'-end of the sequence encode PDGF-BB; and the bases 85-123 from the 5'-end of the sequence encode the sequence of the linking peptide. The SEQ ID NO:9 in the Sequence Listing encodes the amino acid sequence of SEQ ID NO:8 in the Sequence Listing, which is consisted of 150 amino acid residues. The recombinant vector ligated correctly with the sequence was named as pET-CBD-PDGF.

Figure 5:
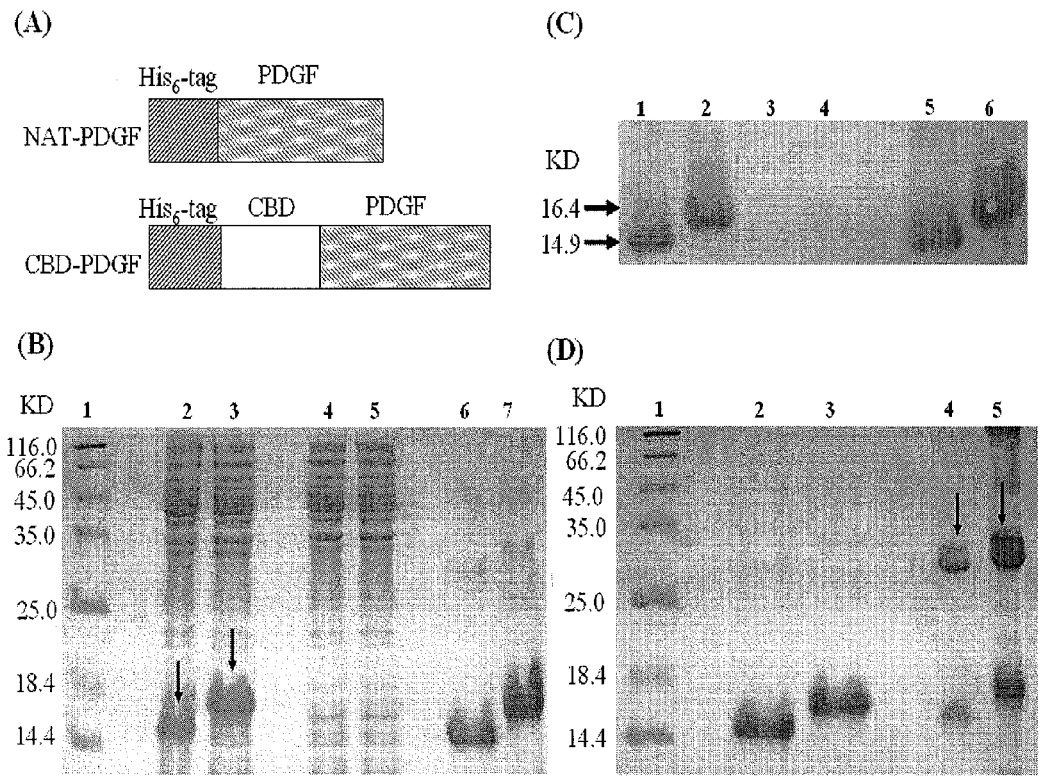
FIG. 5 shows the structural illustration of CBD-PDGF and NAT-PDGF, the SDS-PAGE and Western-blotting results of different forms of CBD-PDGF and NAT-PDGF after expression, and the SDS-PAGE results of CBD-PDGF and NAT-PDGF in the form of inclusion body before and after renaturation.

2. Expression and Purification of the Fused Active Restoration Factor PDGF-BB with the Ability of Specifically Binding to Collagen The prokaryotic expression vector pET-NAT-PDGF having the coding sequence of PDGF-BB mature peptide with the histidine-affinity tag and the prokaryotic expression vector pET-CBD-PDGF having the coding sequence of the histidine-affinity tagged fusion protein comprising the collagen binding domain and the PDGF-BB mature peptide, which were constructed in step 1, were used to transform $E.$ $coli$ BL21 (DE3) competent cells. The transformed cells were spread on the LB plates and cultured at 37° C. Single colonies were picked, inoculated into LB broth, and cultured at 37° C. for 12-24 hours. They were inoculated at 2% ratio into 100 mL LB broth and cultured at 37° C. for 3 hours, until the $OD_{600}$ reached about 0.8. IPTG at the final concentration of 1 mM were added and they were cultured for another 4 hours. After culturing, thallus was harvested by 8000 rpm centrifugation, washed with PBS (NaCl 8.5 g, $Na_2HPO_4$ 2.2 g, $NaH_2PO_4$ 0.4 g dissolved in 100 mL dd$H_2$O, pH7.2), and harvested again by centrifugation after wash. The thallus was resuspended in 10 mL PBS and supersupersonicated, which resulted into the crude extract of the whole recombinant protein. The inclusion body was collected by centrifugation and the protein of inclusion body was obtained through wash and dissolution. The two kinds of inclusion body protein were renatured by dilution, and purified and desalted using the affinity chromatographic column of fixed metal ion ($Ni^{2+}$) ligand (Amersham biosciences), and lyophilized for storage. The expression and purification products of recombinant strain transformed with pET-CBD-PDGF and pET-NAT-PDGF respectively were examined on 15% SDS-PAGE, and the result is shown in Panel B of FIG. 5 (lane 1: the protein Marker; lanes 2, 4, 6: whole bacterial protein, supernatant protein, and inclusion body protein obtained by the induced expression of the recombinant strain transformed with pET-NAT-PDGF respectively; lanes 3, 5, 7: whole bacterial protein, supernatant protein, and inclusion body protein obtained by the induced expression of the recombinant strain transformed with pET-CBD-PDGF respectively; the arrow indicates the target protein in the whole bacterial protein). As can be seen from the panel B of FIG. 5, the recombinant protein, whose molecular weight is about 14.7 KD, was obtained by the induced expression of the recombinant strain transformed with pET-NAT-PDGF, and the recombinant protein, whose molecular weight is about 16.4 KD, was obtained by the induced expression of the recombinant strain transformed with pET-CBD-PDGF, which match the expected result. The target proteins are mainly expressed in the form of inclusion body, and higher purity of target proteins were obtained after purification. The above mentioned expression products were examined by Western-blotting, wherein the primary antibody used for detecting the induced expression product of recombinant strain transformed with pET-NAT-PDGF was mouse anti-polyhistidine monoclonal antibody (Sigma-Aldrich), and the secondary antibody was sheep anti-mouse-alkaline phosphatase antibody (Sigma-Aldrich); the primary antibody used for detecting the induced expression product of recombinant strain transformed with pET-CBD-PDGF was mouse anti-polyhistidine monoclonal antibody (Sigma-Aldrich), and the secondary antibody was sheep anti-mouse-alkaline phosphatase antibody (Sigma-Aldrich). The result is shown in panel C of FIG. 5 (lanes 1, 3, 5: the hybridization result of whole bacterial protein, supernatant protein, and inclusion body protein obtained by the induced expression of the recombinant strain transformed with pET-NAT-PDGF respectively; lanes 2, 4, 6: the hybridization result of whole bacterial protein, supernatant protein, and inclusion body protein obtained by the induced expression of the recombinant strain transformed with pET-CBD-PDGF respectively), which proved that correct target proteins were obtained by induced expression, and further proved that the target proteins are mainly expressed in the form of inclusion body. Finally, the inclusion body proteins before and after renaturation were analyzed on 15% SDS-PAGE, and the result is shown in the panel D of FIG. 5 (Lane 1: protein Marker; Lanes 2 and 4: inclusion body proteins before and after renaturation obtained by induced expression of recombinant strain transformed with pET-NAT-PDGF; Lanes 3 and 5: inclusion body protein before and after renaturation obtained by induced expression of recombinant strain transformed with pET-CBD-PDGF; the arrow indicates the target protein in the dimer form), showing platelet-derived growth factor in form of dimer (active form) with the ability of specifically binding to collagen was obtained, i.e. the fusion protein comprising CBD and PDGF-BB mature peptide with histidine-affinity tag, which was named as CBD-PDGF (its structural illustration is shown in the panel A of FIG. 5). The recombinant $E.$ $coli$ expressing the protein was named as BL21 (DE3)-pET-CBD-PDGF, and the PDGF-BB mature peptide with the histidine-affinity tag was named as NAT-PDGF (its structural illustration is shown in the panel A of FIG. 5).

Figure 6:
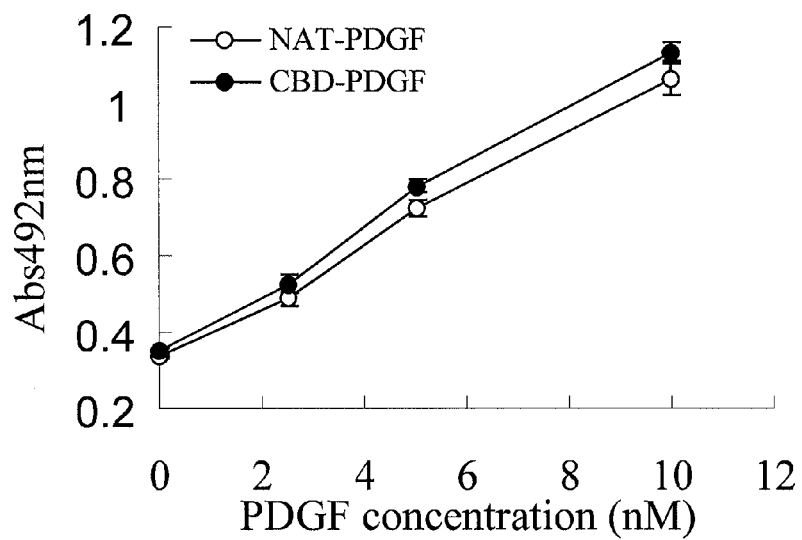
FIG. 6 shows the biological activity test results for CBD-PDGF and NAT-PDGF.

II. Activity Test of the Fused Active Restoration Factor PDGF-BB with the Ability to Specifically Bind to Collagen The activity of CBD-PDGF and NAT-PDGF prepared in step I was tested by MTT experiment and the detailed method is: mouse 3T3 fibroblast (purchased from the cell bank of Peking Union Medical College) was stimulated with CBD-PDGF and NAT-PDGF of 0-12 nM concentration, and the non-stimulated 3T3 cells were used as control. MTT experiment was conducted after 3-day CBD-PDGF and NAT-PDGF treatment respectively, and the result is shown in FIG. 6. The value of $OD_{492}$ increased as the concentrations of CBD-PDGF and NAT-PDGF increased, indicating the number of survival cell increased and showing the dose-dependent effect. And by statistical analysis, there is no significant difference between the experiment results for the two proteins, indicating both the dialysis-renatured proteins CBD-PDGF and NAT-PDGF have the biological activity, but the activity of CBD-PDGF is a little higher than that of NAT-PDGF.

III. Test of the Binding Ability of CBD-PDGF to Collagen

Figure 7:
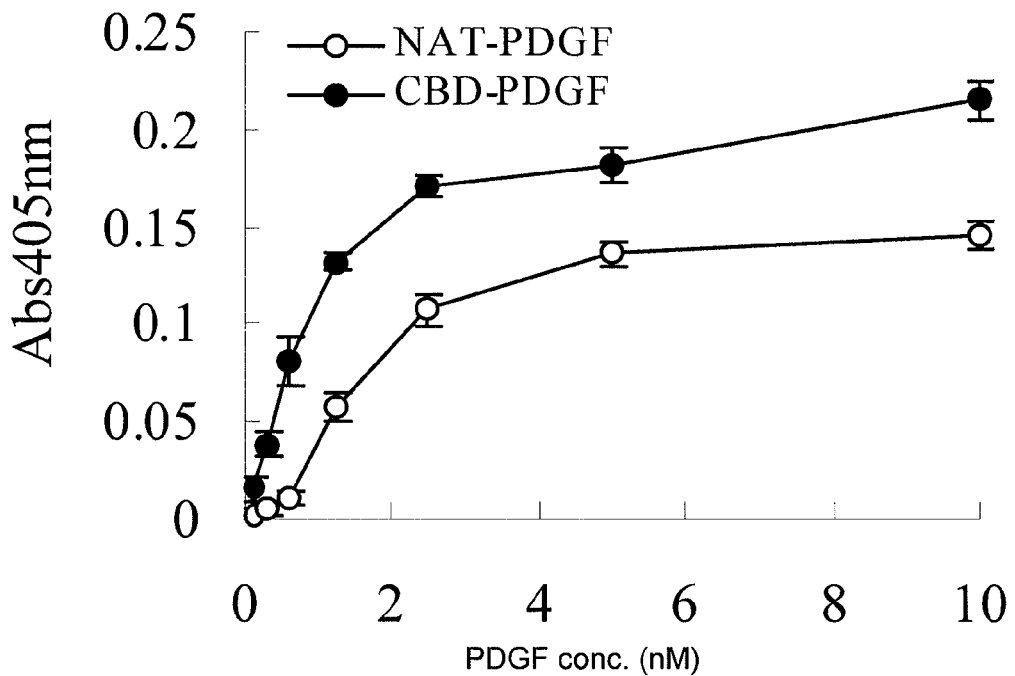
FIG. 7 shows the test results for collagen binding ability of CBD-PDGF and NAT-PDGF.

The binding abilities of CBD-PDGF and NAT-PDGF to collagen membrane were tested by the modified ELISA same as example 1, and the dissociation constants Kd of these two proteins against collagen were calculated. The gradually increasing dose of CBD-PDGF and NAT-PDGF were loaded onto the collagen gel (0.1 mg) made of equal amount of type I collagen. After full absorption, the non-binding protein was washed off with PBS, and the test results of the binding capacity of equal amount of collagen (0.1 mg) to various amounts of CBD-PDGF and NAT-PDGF are shown in FIG. 7 (the horizontal coordinates is the concentration of PDGF soaking the collagen, and the vertical coordinates is the absorbance of samples at 405 nm in the ELISA assay). Under the condition of same loading quantity of protein, the remaining amount of CBD-PDGF on the collagen membrane is significantly higher than that of NAT-PDGF, indicating that the binding efficiency of the former is significantly higher than that of the latter. Furthermore, the dissociation constants Kd of NAT-PDGF and CBD-PDGF are 0.236 nmol and 0.092 nmol respectively. According to the definition of Kd, the lower of the Kd of a protein, the stronger its ability to bind to collagen. The results of the above experiments indicate that the ability of CBD-PDGF to bind to collagen is increased dramatically compared to NAT-PDGF.

IV. The In Vitro Function Assay of CBD-NGF

Figure 8:
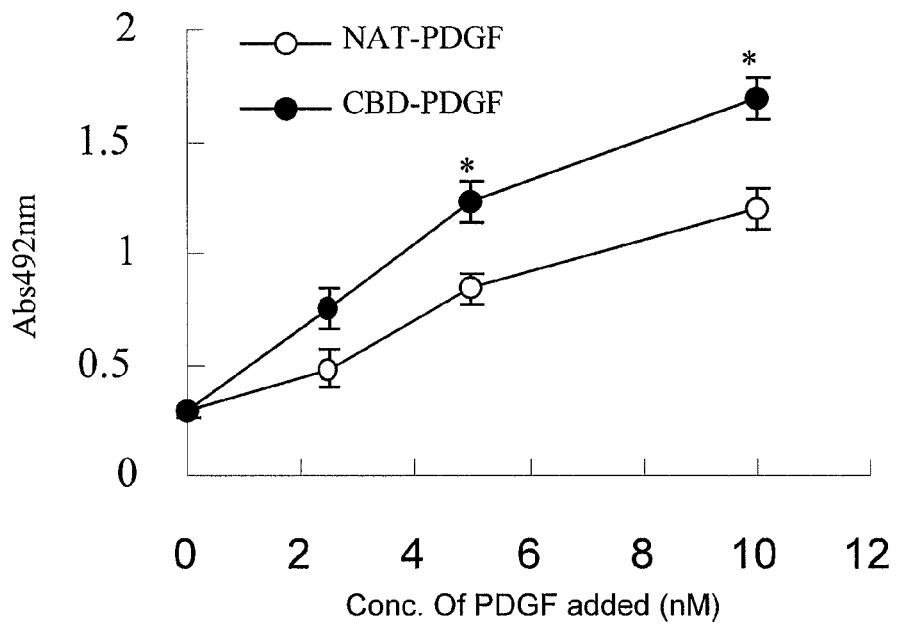
FIG. 8 shows the results of in vitro function assay for CBD-PDGF and NAT-PDGF.

Firstly, the gradually increasing concentration of CBD-PDGF and NAT-PDGF were loaded onto the 48-well plate coated with acidic collagen (from mouse tail) (0.2 mg collagen/well). After 1-hour absorption, the plate was washed twice with PBS, and then mouse 3T3 fibroblast was inoculated in the plate, $5 \times 10^3$ cells each well, and cultured at 37° C. for 3 days. The number of survival cell was tested by MTT method and the result is shown in FIG. 8 (the horizontal coordinates is the concentration of PDGF soaking the collagen, and the vertical coordinates is the absorbance of samples at 492 nm in the MTT assay). The value of $OD_{492}$ increased as the concentrations of PDGF increased, indicating the number of survival cell increased. The experimental results of two proteins above show the dose-dependent effect. And by statistical analysis, there is significant difference between the experiment results for the two proteins (*: $p<0.05$). Compared to NAT-PDGF, CBD-PDGF has higher activity on the collagen, and can promote the survival and growth of PC12 cells better.

V. The In Vivo Function Test of CBD-PDGF Loaded on Collagen

Figure 9A:
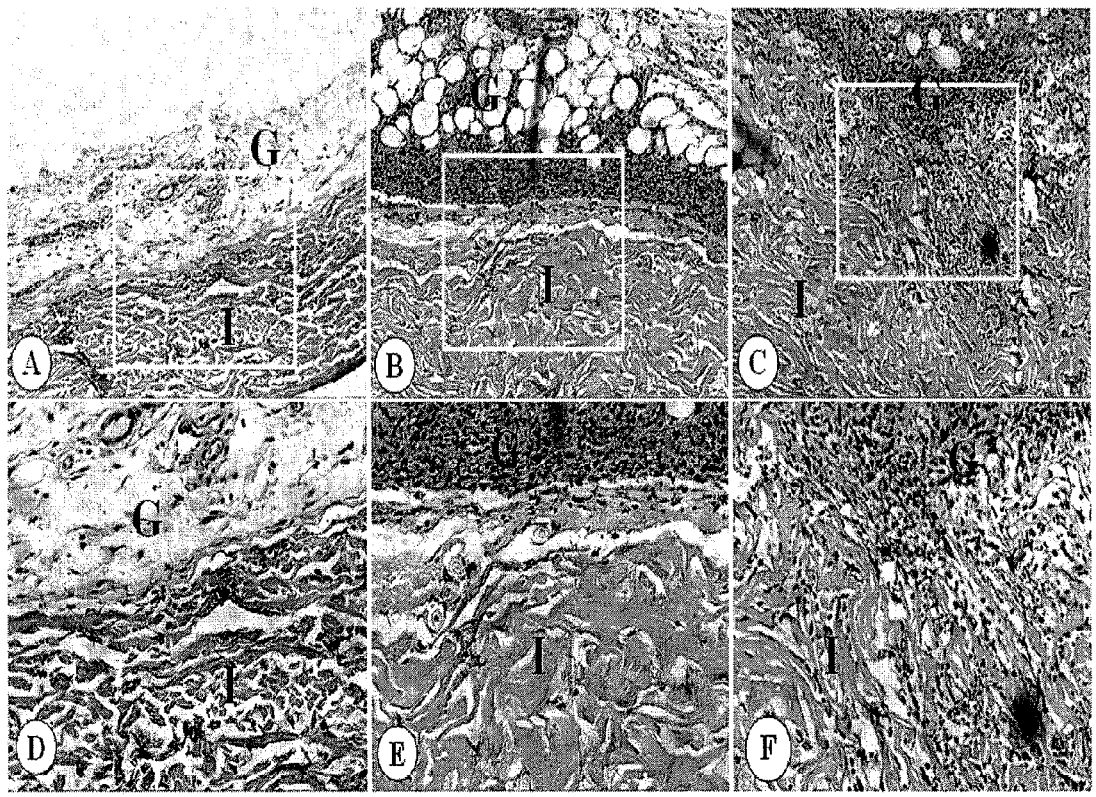
FIG. 9A shows the observation results for cellularization of the collagen materials loaded with CBD-PDGF and NAT-PDGF, respectively, which were transplanted to the injury site of rats with the whole skin of back removed.
Figure 9B:
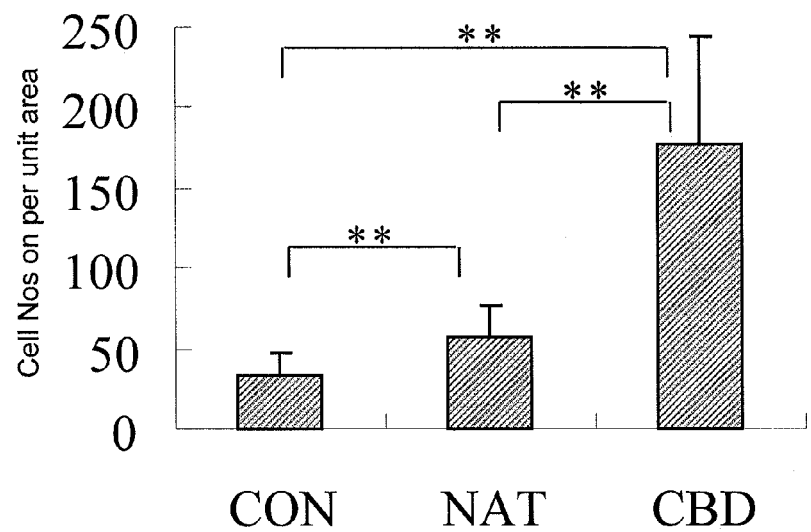
FIG. 9B shows the statistical results of the cell number on the collagen materials loaded with CBD-PDGF and NAT-PDGF, respectively, which were transplanted to the injury site of rats with the whole skin of back removed.

After 10 nmol of NAT-PDGF and CBD-PDGF were respectively loaded onto the collagen scaffold made of type I collagen (60 mg) (loading quantity of 0.167 nmol/mg collagen), the collagen scaffold was transplanted to the injury site of rats with whole skin of back removed for observing the cellularization of the material, and the control group (CON) is free of PDGF. The result is shown in FIGS. 9 ((A) and (D) are control group; (B) and (E) are NAT-PDGF plus collagen group; (C) and (F) are CBD-PDGF plus collagen group. G=granulation tissue, I=transplanted collagen material; Panel A, B, and C are the observation results of 10×10 magnification; Panel D, E, and F are the observation results of 10×20 magnification). As can be seen from FIG. 9A, compared with the control and NAT-PDGF groups, lots of cells migrated to the inside of the material under the effect of CBD-PDGF. Statistical analysis were performed on the cell density (cell/mm²) on collagen material of the three groups, and the results are shown in FIG. 9B (CON=collagen alone; NAT=NAT-PDGF plus collagen group; CBD=CBD-PDGF plus collagen group). There is significant difference among the cell density on the collage material of three groups (*: $p<0.05$, **: $p<0.01$). The cell density of collagen material loaded with CBD-PDGF is significantly higher than those of other two groups, indicating CBD-PDGF can better promote cell proliferation and wound healing in vivo.

EXAMPLE 4

Cloning, Expression, Purification and Function Identification of the Gene Encoding the Fused Active Restoration Factor bFGF (Basic Fibroblast Growth Factor) Which has the Ability to Specifically Bind to Collagen I. Cloning, Expression and Purification of the Gene Encoding the Fused Active Restoration Factor bFGF Which has the Ability to Specifically Bind to Collagen 1. Cloning of the Gene Encoding the Fused Active Restoration Factor bFGF Which has the Ability to Specifically Bind to Collagen and Construction of Its Expression Vector 1) Primer Design Three forward primers (CBDU, FGFU12, and FGFU22, referring to Table 2 for their sequences) and two reverse primers (CBDD and FGFD2, referring to Table 2 for their sequences) were designed using Primer premier 5.05 software, wherein CBDU (introducing a recognition site of restriction endonuclease NdeI) and CBDD (introducing a recognition site of restriction endonuclease HindIII) were used to amplify the coding sequences of collagen binding domain and the linking peptide (LINKER), wherein the conserved amino acid sequence of collagen binding domain is TKKTLRT (SEQ ID NO:1 in the Sequence Listing) and the amino acid sequence of the linking peptide is GSAG-SAAGSGGK (SEQ ID NO: 24); FGFU12 (introducing a recognition site of restriction endonuclease NdeI) and FGFD2 (introducing a stop codon and a recognition site of restriction endonuclease Xho I) were used to amplify the coding sequence of bFGF; FGFU22 (introducing a recognition site of restriction endonuclease HindIII) and FGFD1 (introducing a stop codon and a recognition site of restriction endonuclease Xho I) were also used to amplify the coding sequence of bFGF.

TABLE 3

Primer Sequences

CBDU:
(SEQ ID NO: 19)
5'-ATC<u>CATATG</u>ACTAAGAAAACCCTGCGTACTGGTAGCGCGGGCAGT-3'
(the underlined bases is the recognition site of restriction endonuclease Nde I)

CBDD:
(SEQ ID NO: 20)
5'-ACT<u>AAGCTT</u>ACCGCCAGAACCCGCAGCACTGCCCGCGCTACCAGT-3'
(the underlined bases is the recognition site of restriction endonuclease Hind III)

TABLE 3-continued

Primer Sequences

FGFU12:
(SEQ ID NO: 28)
5'-GGTACCGGTAGCGCGGGCAGT-3'
(the underlined bases is the recognition site of
restriction endonuclease Hind III)

FGFU22:
(SEQ ID NO: 29)
5'-GTCGACgcagccgggagcatcaccacg-3'
(the underlined bases is the recognition site of
restriction endonuclease Hind III)

FGFD2:
(SEQ ID NO: 30)
5'-CTCGAGGCTCTTAGCAGACATTGGAAGAAAA-3'
(the underlined bases is the recognition site of
restriction endonuclease Hind III)

2) The PCR Amplification of the Coding Sequence of the Fused Active Restoration Factor bFGF with the Ability of Specifically Binding to Collagen, and the Construction of Its Expression Vector CBDU and CBDD were used mutually as templates, the coding sequences of collagen binding domain and the linking peptide were amplified by the overlap extension PCR technique, wherein 50 μl PCR reaction system contained: 1 pmol/μl of each of primer CBDU and CBDD, 200 μmol/μl dNTPs, 1 μl Taq polymerase, adding ddH$_2$O to 50 μl. The PCR reaction condition was: predenaturation at 94° C. for 5 min; then denaturation at 94° C. for 30 sec, annealing at 55° C. for 1 min, extension at 72° C. for 1 min, 30 cycles; final extension at 72° C. for 10 min. At the end of the reaction, the PCR amplification product was analyzed by electrophoresis on 1.5% agarose gel, which resulted into a band about 70 bp. After the target band was recovered and purified, it was double digested with restriction endonucleases Nde I and Hind III and then ligated with the prokaryotic expression vector pET28a (Novagen co.) which was double digested with the same endonucleases. The recombinant vector was sequenced and the result indicated that the correct coding sequences of collagen binding domain and the linking peptide were obtained. The recombinant vector ligated correctly with the sequence was named as pET-CBD.

Figure 10:
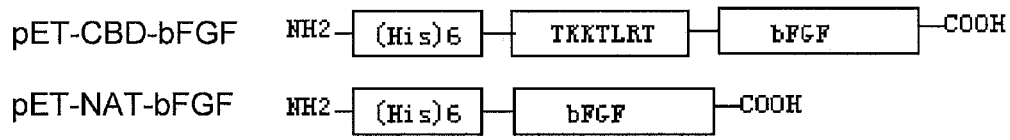
FIG. 10 shows the partial structural illustration of vectors pET-NAT-bFGF and pET-CBD-bFGF.

Using the full length cDNA of bFGF gene (GenBank Assession No. NM_002006) as the template, bFGF gene was amplified with the primer pairs of FGFU12 and FGFD2, as well as FGFU22 and FGFD2. The 50 μl PCR reaction system was: 1 pmol/μl of each of upstream and downstream primers, 200 μmol/μl dNTPs, 1 μl Taq polymerase, adding ddH$_2$O to 50 μl. The PCR reaction condition was: predenaturation at 94° C. for 5 min; denaturation at 94° C. for 45 s, annealing at 55° C. for 1 min, extension at 72° C. for 1 min, 30 cycles; finally 72° C. for 10 min for adequate extension. At the end of the reaction, the PCR amplification product was analyzed by electrophoresis on 1.5% agarose gel, which resulted into two bands about 500 bp. After the two target bands were recovered and purified, the amplified bands of FGFU12 and FGFD2 primers was double digested with Nde I and Xho I and ligated with the prokaryotic expression vector pET28a which was double digested with the same endonucleases. The recombinant vector was sequenced and the result indicates that the correct coding sequence of bFGF mature peptide with the histidine-affinity tag was obtained. It has the nucleotide sequence of SEQ ID NO:15 in the Sequence Listing, which is consisted of 525 nucleotides, encoding the amino acid sequence of SEQ ID NO:14 in the Sequence Listing, which is consisted of 175 amino acid residues. The recombinant vector ligated correctly with the sequence was named as pET-NAT-bFGF, its partial structural illustration is shown in FIG. 16. Meanwhile the amplified band of FGFU12 and FGFD2 primers was double digested with Hind III and Xho I, and ligated with the prokaryotic expression vector pET-CBD which was double digested with the same endonucleases. The recombinant vector was sequenced and the result indicated that the correct coding sequence of the histidine-affinity tagged fusion protein comprising collagen binding domain "TKK-TLRT" and bFGF mature peptide was obtained. The said sequence has the nucleotide sequence of SEQ ID NO:13 in the Sequence Listing, which is consisted of 591 bases. The bases 13-30 from the 5'-end of the sequence encode the sequence of histidine-affinity tag; the bases 64-84 from the 5'-end of the sequence encode the conserved sequence of collagen binding domain; the bases 130-591 from the 5'-end of the sequence encode bFGF; and the bases 91-123 from the 5'-end of the sequence encode the sequence of the linking peptide. The SEQ ID NO:13 in the Sequence Listing encodes the amino acid sequence of SEQ ID NO:12 in the Sequence Listing, which is consisted of 197 amino acid residues. The recombinant vector ligated correctly with the sequence was named as pET-CBD-bFGF, its partial structural illustration is shown in FIG. 10.

Figure 11A:
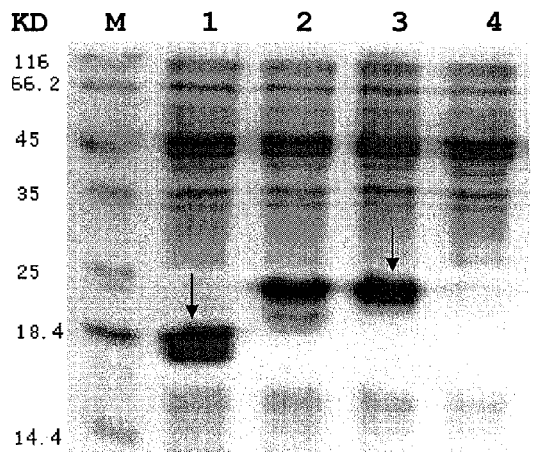
FIG. 11A shows the SDS-PAGE test results for whole bacterial proteins from the recombinant strains after their expression by induction, the recombinant strains transformed with pET-NAT-bFGF, pET-28a-bFGF-v, and pET-CBD-bFGF, respectively.
Figure 11B:
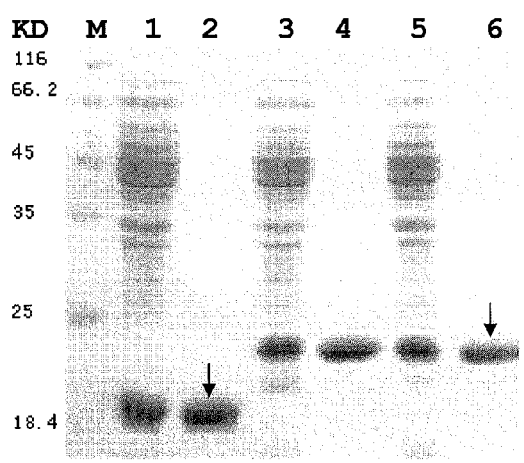
FIG. 11B shows the SDS-PAGE test results for the lysate supernatant obtained from recombinant strain after their expression by induction and the purified proteins of interest therefrom, the recombinant strains transformed with pET-NAT-bFGF and pET-CBD-bFGF, respectively.

2. Expression and Purification of the Special Fused Active Restoration Factor bFGF with the Ability of Specifically Binding to Collagen The prokaryotic expression vector pET-NAT-bFGF having the coding sequence of bFGF mature peptide with the histidine-affinity tag and the prokaryotic expression vector pET-CBD-bFGF having the coding sequence of the fusion protein comprising the collagen binding domain and the bFGF mature peptide with the histidine-affinity tag, which were constructed in step 1, were used to transform E. coli BL21 (DE3) competent cells. The E. coli BL21 (DE3) transformed with pET-28a empty vector was used as control. The transformed cells were spread on the LB plates and cultured at 37° C. Single colonies were picked up, inoculated into LB broth, and cultured at 37° C., 200 rpm for 12-24 hours. They were inoculated at 2% ratio into 100 mL LB broth and cultured at 37° C., 200 rpm for 3 hours, until the OD$_{600}$ reached about 0.8. IPTG at the final concentration of 1 mM were added and they were cultured at 25° C., 200 rpm for another 8 hours. After culturing, thallus was harvested by 8000 rpm centrifugation for 10 min, and harvested again by centrifugation after wash with PBS (NaCl 8.5 g, Na$_2$HPO$_4$ 2.2 g, NaH$_2$PO$_4$ 0.4 g dissolved in 100 mL ddH$_2$O, pH7.2). The thallus was stored at −80° C. or directly supersonicated after culturing. The supernatant and pellet were isolated by centrifugation, and the target protein is about half in the supernatant and the pellet respectively. The supernatant was used as the source for isolating target protein, and the affinity chromatographic column of fixed metal ion (Ni$^{2+}$) ligand (Amersham biosciences) was used for purification. The purified expression product was renatured by dialysis, and concentrated by ultra-filtration. The protein solution system was then exchanged with 50 mM MES buffer (purchased from GIBCO), and kept at 4° C. after being lyophilized. The whole bacterial protein and purified product from supernatant were analyzed on 15% SDS-PAGE, and the test result of whole bacterial protein is shown in FIG. 11A (lane M: protein Marker; lanes 1 and 3: whole bacterial protein obtained by induced expression of the recombinant strain transformed with pET-NAT-bFGF and pET-CBD-bFGF respectively; lane 4: whole bacterial protein obtained by induced expression of the recombinant strain transformed with pET-28a empty vector as a negative control; the arrow in the Figure indicates the target protein). As can be seen from the FIG. 11A, the recombinant protein of molecular weight being about 19 KD was obtained by the induced expression of the recombinant strain transformed with pET-NAT-bFGF and the recombinant protein of molecular weight being about 21 KD was obtained by the induced expression of the recombinant strain transformed with pET-CBD-bFGF, which match the expected result. The test results of bacteria lysate supernatant and the target protein purified therefrom are shown in FIG. 11B (lane M is protein marker; lanes 1 and 5: lysate supernatant obtained from the recombinant strain transformed with pET-NAT-bFGF and pET-CBD-bFGF after induced expression respectively; lanes 2 and 6: target protein purified from the supernatant obtained from the recombinant strain transformed with pET-NAT-bFGF and pET-CBD-bFGF after induced expression respectively; the arrow indicates the target protein). As can be seen from FIG. 11B, relatively higher purity of target protein is obtained from the lysate supernatant. The 21 KD fusion protein comprising collagen binding domain "TKKTLRT" and bFGF mature peptide with histidine-affinity tag was named as C-bFGF, and the recombinant E. coli expressing the protein was named as BL21(DE3)-pET-C-bFGF, and the expressed bFGF mature peptide with histidine-affinity tag was named as NAT-bFGF.

II. Test for the Collagen Binding Ability of C-bFGF

Figure 12:
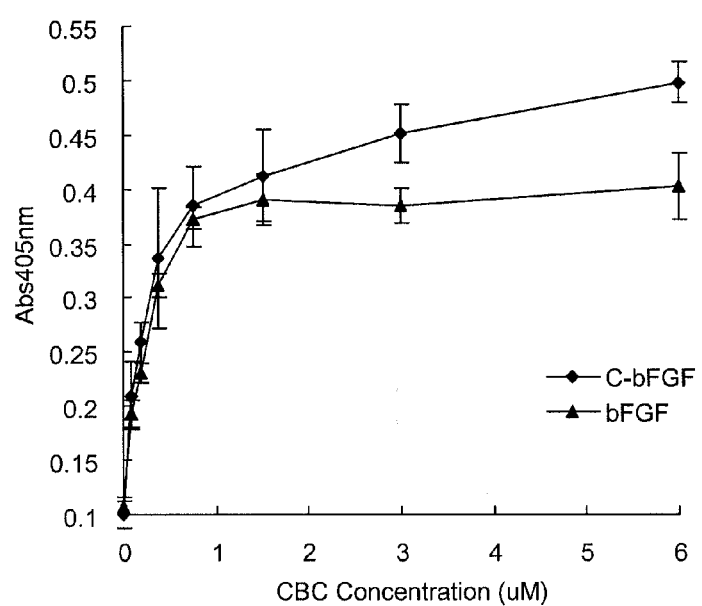
FIG. 12 shows the test results for the collagen binding ability of C-bFGF.

The binding ability of various concentrations (1-6 µM) of C-bFGF and NAT-bFGF (control) to collagen membrane was tested by the modified ELISA same as example 1. A gradually increasing dose of C-bFGF and NAT-bFGF were loaded onto the collagen membrane made of equal amount of acidic collagen (derived from rat tails) (6.0 mg). After fully absorption, the non-binding protein was washed off with PBS. The test results for the binding capacity of equal amount of collagen (6.0 mg) to various amounts of C-bFGF and NAT-bFGF are shown in FIG. 12 (the horizontal coordinate represents the concentration of bFGF for soaking the collagen, and the vertical coordinate represents the absorbance at 405 nm of samples in the ELISA assay). In the case of the same loading quantity of proteins, the remaining amount of C-bFGF on the collagen membrane is significantly higher than that of NAT-bFGF (*: p<0.05), indicating that the binding efficiency of C-bFGF is significantly higher than that of NAT-bFGF.

Figure 13:
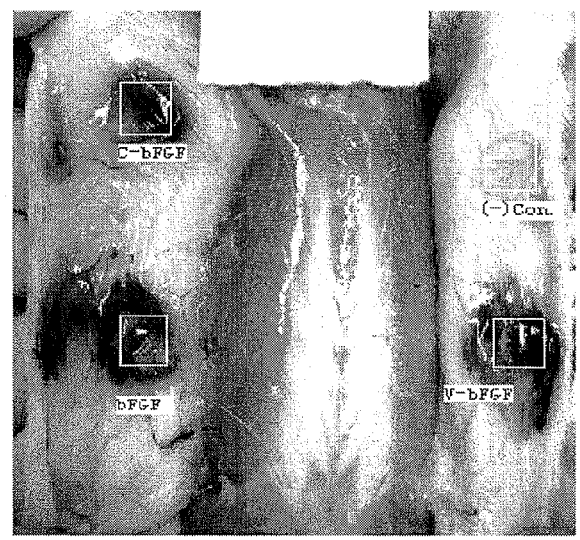
FIG. 13 shows the test for the proangiogenic effects of complexes after 4-day subcutaneous embedment, the complexes formed by C-bFGF and NAT-bFGF with collagens, respectively.

III. Tests for Directional Proangiogenic Effects of C-bFGF and NAT-bFGF at Local Rat Skin First, equal amount (580 pmol) of C-bFGF and NAT-bFGF were combined with fibrosis collagen membrane (Zhenghai Biotechnology CO. Ltd.) of the same size respectively, the collagen membrane without bFGF loading used as negative control (Con), and then embedded subcutaneously into the skin of healthy adult male Wistar rats. After 4 days, the skin was cut off for detecting their local proangiogenic effects. The result is shown in FIG. 13 (the squares indicate the location of collagen). NAT-bFGF without collagen binding domain diffuses more easily, causing vascularization of surrounding tissues, whereas C-bFGF can better locate on the collagen material, where the vascularization effect is significant, indicating that the collagen binding ability of bFGF is in positive correlation with the directionality of its proangiogenic effect. The directional proangiogenic effect of C-bFGF on local rat skin is significantly superior to bFGF.

Figure 14:
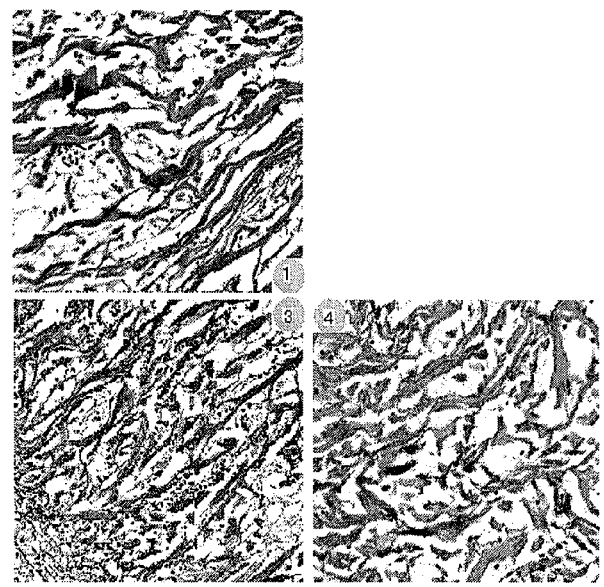
FIG. 14 shows the observation results for cellularization of the collagen materials loaded with C-bGF and NAT-bFGF, respectively, which were transplanted to the injury site of rats with the whole skin of back removed.
Figure 15:
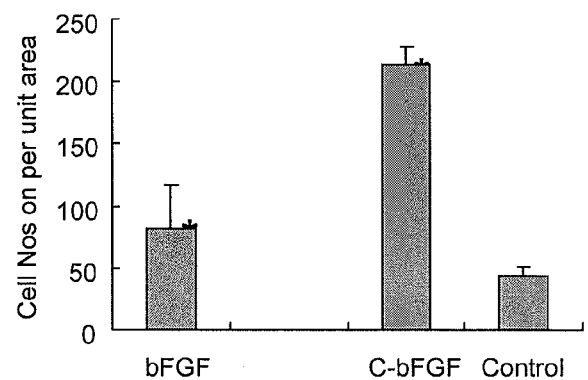
FIG. 15 shows the statistical results of the cell number on the collagen materials loaded with C-bFGF and NAT-bFGF, respectively, which were transplanted to the injury site of rats with the whole skin of back removed.

IV. Histological Analysis for the In Vivo Cellularization on Collagen Materials Loaded with C-bFGF and NAT-bFGF Respectively After C-bFGF and NAT-bFGF were loaded onto the collagen scaffold (a loading quantity of 120 pmol/mg collagen) made of type I collagen (6.0 mg), they were transplanted to the injury site of rats with whole skin of back removed, collagen materials without bFGF loading as control. After about 7 days, grafts and corresponding skins were removed from the transplanted site, fixed with formalin, embedded with paraffin and sliced. Cellularization was observed using hematoxylin-eosin stain (H&E stain), groups without bFGF loading as control. Results are shown in FIG. 14 ((brown) red spongy substance represents collagen membrane, blue points represent cell nucleus. 1: NAT-bFGF group, 3: C-bFGF group, 4: blank control group). As can be seen in FIG. 14, compared to control and NAT-bFGF groups, a number of cells migrated to the inside of the material under the action of C-bFGF. Statistical analysis was performed on the cell density (cell/mm$^2$) on the collagen materials of the three groups. The result is shown in FIG. 15 (Control=collagen alone; bFGF=NAT-bFGF+collagen group; C-bFGF=C-bFGF+collagen group). There is significant difference in the cell density on the collage materials of the four groups (*: p<0.05). The cell density of collagen material loaded with C-bFGF is significantly higher than the other two groups, indicating that C-bFGF of the present invention can better promote cell proliferation and wound heal in vivo, compared to bFGF without collagen binding domain.

INDUSTRIAL APPLICABILITY

The fused active restoration factor with the ability of specifically binding to collagen provided in the present invention is contemplated from the view of modifying cytokines. Fusing a collagen binding domain (CBD) to the N-terminus or C-terminus of cytokines or their functional subunits enhances the binding between cytokines or their functional subunits and collagen, creating a relative stronger physiochemical force between cytokines and collagens so that cytokines or their subunits are allowed to be anchored to the collagen, establishing a relative higher concentration at the action site. In this way, equivalent activities can be maintained while dramatically reducing the amount of cytokines or their subunits, avoiding the risks caused by high dosage. The enriched cytokines can also avoid the negative effects on tissues caused by free diffusion, achieving the directional restoration of a specific tissue. The preparation method of the present invention is simple and convenient, useful for a large scale of industrial production, and will play a vital role in the fields of injury restoration, such as skin injury, nerve injury, or bone damage, with a broad perspective of clinical applications.

What is claimed is:

1. A fused active restoration factor used to activate collagen scaffold materials, comprising a fusion protein obtained by fusing a collagen binding domain to the amino terminus or carboxyl terminus of a cytokine, wherein the collagen binding domain is a polypeptide consisting of 7-27 amino acid residues, wherein the amino acid sequence of the fused active restoration factor is shown as set forth in SEQ ID NO: 12 in the sequence list.

2. The fused active restoration factor according to claim 1, wherein the amino terminus of the fused active restoration factor is linked to a histidine-affinity tag sequence consisting of 6 histidine residues.

3. An activated collagen restoration material which is a collagen loaded with the fused active restoration factor according to claim 1.

4. The collagen restoration material according to claim 3, wherein the loading quantity of the fused active restoration factor is 1-4000 pmol protein/mg collagen.

5. A method for expressing a fused active restoration factor comprising: constructing a recombinant expression vector containing a nucleic acid that encodes the fused active restoration factor of claim 1; transforming the constructed recombinant expression vector into a host cell; culturing the host cell to express the fused active restoration factor; and obtaining the fused active restoration factor.

6. The method according to claim 5, wherein the initial vector for constructing the recombinant expression vector is pET-28a, pET-28b, pET-28c, pET-21a(+) or pET-30a.

7. The method according to claim 6, wherein the recombinant expression vector is pET-CBD-bFGF.

8. The method according to claim 5, wherein the host is *E. coli* BL21(DE3), *E. coli* BL21(DE3)plys, *E. coli* BLR(DE3) or *E. coli* B834, and the recombinant strain constructed with *E. coli* BL21(DE3) as a host is BL21(DE3)-pET-CBD-bFGF.

9. The method according to claim 5, wherein culturing the host cell comprises culturing a recombinant *E. coli* host cell at a temperature of 35-39° C. for an induction period of 2-4 hours in the presence of 0.8-1.2 mmol/L IPTG inducer.

10. A method of preparing a restoration material for animal tissues, the method comprising the step of activating a collagen scaffold material with the fused active restoration factor of claim 1.

11. The method according to claim 10, wherein the restoration material for animal tissues is injury restoration material, nerve injury restoration material, or bone damage restoration material.

* * * * *